(12) United States Patent
Lindner et al.

(10) Patent No.: US 11,090,407 B2
(45) Date of Patent: Aug. 17, 2021

(54) THERMOPLASTIC POLYMERIC MATERIALS WITH HEAT ACTIVATABLE COMPOSITIONS

(71) Applicant: The Procter & Gamble Company, Cincinnati, OH (US)

(72) Inventors: Torsten Lindner, Kronberg (DE); Holger Beruda, Schwalbach am Taunus (DE); Jon Brennan, Owensboro, KY (US); Gueltekin Erdem, Hessen (DE); Franz Josef Lanyi, Erlangen (DE); Dirk Wolfram Schubert, Eggolsheim (DE)

(73) Assignee: The Procter & Gamble Company, Cincinnati, OH (US)

( * ) Notice: Subject to any disclaimer, the term of this patent is extended or adjusted under 35 U.S.C. 154(b) by 576 days.

(21) Appl. No.: 15/916,466

(22) Filed: Mar. 9, 2018

(65) Prior Publication Data

US 2018/0256773 A1  Sep. 13, 2018

Related U.S. Application Data

(60) Provisional application No. 62/469,155, filed on Mar. 9, 2017.

(51) Int. Cl.
*A61F 13/15* (2006.01)
*A61L 15/60* (2006.01)
(Continued)

(52) U.S. Cl.
CPC ............. *A61L 15/60* (2013.01); *A61F 13/511* (2013.01); *A61F 13/5116* (2013.01);
(Continued)

(58) Field of Classification Search
CPC ........ A61L 15/60; A61L 15/24; A61F 13/511; A61F 13/5116; A61F 2013/51028;
(Continued)

(56) References Cited

U.S. PATENT DOCUMENTS 3,093,612 A   6/1963  Cox
3,139,412 A   6/1964  Sterling
(Continued)

FOREIGN PATENT DOCUMENTS

EP   0735089 A2   10/1996
EP   862402       9/1998
(Continued)

OTHER PUBLICATIONS

International Search Report for PCT/US2017/021522, dated May 19, 2017.
(Continued)

*Primary Examiner* — Jacqueline F Stephens
(74) *Attorney, Agent, or Firm* — George H. Leal

(57) ABSTRACT

A permeable nonwoven web having a plurality of fibers and/or filaments of a first polymer matrix forming an outer surface of each of the plurality of fibers and/or filaments is described herein. The first polymer matrix includes a hydrophilic melt additive and/or a tactile modifying melt additive blended therein. Energy application across the entirety of the web, or parts thereof, promotes the blooming of the melt additive from the first polymer matrix such that bloom areas are disposed on at least a portion of each of the outer surfaces of the fibers and/or filaments.

18 Claims, 9 Drawing Sheets

(51) Int. Cl.
  *B01J 20/26* (2006.01)
  *B01J 20/28* (2006.01)
  *A61F 13/511* (2006.01)
  *A61L 15/24* (2006.01)
  *D04H 3/147* (2012.01)
  *D04H 1/482* (2012.01)
  *A61F 13/51* (2006.01)

(52) U.S. Cl.
  CPC ............ *A61L 15/24* (2013.01); *B01J 20/261* (2013.01); *B01J 20/28023* (2013.01); *D04H 1/482* (2013.01); *D04H 3/147* (2013.01); *A61F 2013/5103* (2013.01); *A61F 2013/51028* (2013.01); *A61F 2013/51033* (2013.01)

(58) Field of Classification Search
  CPC .... A61F 2013/5103; A61F 2013/51033; B01J 20/28023; B01J 20/261; D04H 1/482; D04H 3/147
  See application file for complete search history.

(56) References Cited

U.S. PATENT DOCUMENTS

| | | | |
|---|---|---|---|
| 3,423,491 | A | 1/1969 | McLain |
| 3,785,918 | A | 1/1974 | Kawai et al. |
| 3,870,567 | A | 3/1975 | Palmer et al. |
| 4,020,230 | A | 4/1977 | Mahoney et al. |
| 4,304,234 | A | 12/1981 | Hartmann |
| 4,578,414 | A | 3/1986 | Sawyer et al. |
| 4,666,763 | A | 5/1987 | King et al. |
| 4,818,594 | A | 4/1989 | Albien et al. |
| 4,874,567 | A | 10/1989 | Lopatin et al. |
| 5,045,387 | A | 9/1991 | Schmalz |
| 5,198,292 | A | 3/1993 | Lerner et al. |
| 5,283,023 | A | 2/1994 | Nohr et al. |
| 5,300,167 | A | 4/1994 | Nohr et al. |
| 5,593,768 | A | 1/1997 | Gessner |
| 5,593,778 | A * | 1/1997 | Kondo .................. C08G 63/60 264/239 |
| 5,653,930 | A | 8/1997 | Noda et al. |
| 5,667,750 | A | 9/1997 | Nohr et al. |
| 5,780,368 | A | 7/1998 | Noda et al. |
| 5,969,026 | A | 10/1999 | Mor et al. |
| 6,117,801 | A | 9/2000 | McGinty et al. |
| 6,203,889 | B1 | 3/2001 | Quincy, III et al. |
| 6,300,258 | B1 | 10/2001 | Stano et al. |
| 6,353,149 | B1 | 3/2002 | Stone |
| 6,509,092 | B1 * | 1/2003 | Dugan .................. A61L 15/225 428/364 |
| 6,602,386 | B1 | 8/2003 | Takeuchi et al. |
| 6,686,303 | B1 | 2/2004 | Haynes et al. |
| 6,699,806 | B1 | 3/2004 | Takeuchi et al. |
| 6,713,011 | B2 | 3/2004 | Chu et al. |
| 6,746,755 | B2 | 6/2004 | Morrison et al. |
| 6,746,766 | B2 | 6/2004 | Bond et al. |
| 6,767,498 | B1 | 7/2004 | Talley, Jr. et al. |
| 6,818,295 | B2 | 11/2004 | Bond et al. |
| 6,855,422 | B2 | 2/2005 | Magill et al. |
| 6,890,649 | B2 | 5/2005 | Hobbs et al. |
| 6,890,872 | B2 | 5/2005 | Bond et al. |
| 6,946,506 | B2 | 9/2005 | Bond et al. |
| 7,150,912 | B2 | 12/2006 | Mizutani et al. |
| 7,241,497 | B2 | 7/2007 | Magill et al. |
| 7,267,789 | B2 | 9/2007 | Chhabra et al. |
| 7,271,209 | B2 | 9/2007 | Li et al. |
| 7,291,300 | B2 | 11/2007 | Chhabra et al. |
| 7,781,353 | B2 | 8/2010 | Snowden et al. |
| 7,981,226 | B2 | 7/2011 | Pourdeyhimi et al. |
| 8,026,188 | B2 | 9/2011 | Mor |
| 8,168,550 | B2 | 5/2012 | Collias et al. |
| 8,173,553 | B2 | 5/2012 | Aoki et al. |
| 2001/0008965 | A1 | 7/2001 | Kinn et al. |
| 2002/0168912 | A1 | 11/2002 | Bond et al. |
| 2002/0169429 | A1 | 11/2002 | Li et al. |
| 2003/0091803 | A1 | 5/2003 | Bond et al. |
| 2003/0178166 | A1 | 9/2003 | Takeuchi et al. |
| 2003/0203695 | A1 | 10/2003 | Polanco et al. |
| 2004/0005457 | A1 | 1/2004 | DeLucia et al. |
| 2004/0119207 | A1 | 6/2004 | Stone et al. |
| 2004/0127128 | A1 | 7/2004 | Thomas |
| 2004/0161994 | A1 | 8/2004 | Arora et al. |
| 2004/0170816 | A1 | 9/2004 | Watanabe et al. |
| 2004/0192818 | A1 | 9/2004 | Oriani et al. |
| 2005/0095695 | A1 | 5/2005 | Shindler et al. |
| 2005/0130539 | A1 | 6/2005 | Allen et al. |
| 2006/0008643 | A1 | 1/2006 | Lin et al. |
| 2006/0147804 | A1 | 7/2006 | Yamamoto et al. |
| 2006/0154548 | A1 | 7/2006 | Sheehan et al. |
| 2006/0172641 | A1 | 8/2006 | Hennige et al. |
| 2007/0077427 | A1 | 4/2007 | Dugan |
| 2007/0082573 | A1 | 4/2007 | Noda et al. |
| 2007/0232179 | A1 | 10/2007 | Polat et al. |
| 2007/0232180 | A1 | 10/2007 | Polat et al. |
| 2008/0045638 | A1 | 2/2008 | Chapman et al. |
| 2008/0070994 | A1 | 3/2008 | Li et al. |
| 2008/0179777 | A1 | 7/2008 | Wild et al. |
| 2010/0024281 | A1 | 2/2010 | Lemke et al. |
| 2010/0028638 | A1 | 2/2010 | Reichardt et al. |
| 2010/0041292 | A1 | 2/2010 | Kim et al. |
| 2010/0272938 | A1 | 10/2010 | Mitchell et al. |
| 2010/0322989 | A1 | 12/2010 | Martin |
| 2010/0330861 | A1 | 12/2010 | Mor |
| 2011/0104419 | A1 | 5/2011 | Barnholtz et al. |
| 2011/0117176 | A1 | 5/2011 | Klun et al. |
| 2011/0130430 | A1 | 6/2011 | Sonneck et al. |
| 2011/0196332 | A1 | 8/2011 | Cheng et al. |
| 2012/0077886 | A1 * | 3/2012 | Scholz .................. A61L 31/048 514/772.4 |
| 2012/0100772 | A1 | 4/2012 | Hummelgaard et al. |
| 2012/0109090 | A1 | 5/2012 | Reichardt et al. |
| 2012/0122363 | A1 | 5/2012 | Owens |
| 2012/0204760 | A1 | 8/2012 | Puhala et al. |
| 2012/0296036 | A1 | 11/2012 | Allen et al. |
| 2012/0321869 | A1 | 12/2012 | Allen et al. |
| 2012/0321870 | A1 | 12/2012 | Allen et al. |
| 2012/0321871 | A1 | 12/2012 | Bond et al. |
| 2012/0328804 | A1 | 12/2012 | Allen et al. |
| 2013/0004691 | A1 | 1/2013 | Allen et al. |
| 2013/0012093 | A1 | 1/2013 | Bond et al. |
| 2013/0053478 | A1 | 2/2013 | Bond et al. |
| 2013/0053480 | A1 | 2/2013 | Allen et al. |
| 2013/0053901 | A1 | 2/2013 | Cormier et al. |
| 2013/0089747 | A1 | 4/2013 | Allen, Jr. et al. |
| 2013/0158169 | A1 | 6/2013 | Bond et al. |
| 2014/0087941 | A1 | 3/2014 | Allen, Jr. et al. |
| 2014/0272261 | A1 | 9/2014 | Udengaard et al. |
| 2014/0272359 | A1 | 9/2014 | Cheng et al. |
| 2014/0276512 | A1 | 9/2014 | Cheng et al. |
| 2016/0067118 | A1 | 3/2016 | Hammons et al. |
| 2016/0166443 | A1 * | 6/2016 | Arora .................. A61F 13/5126 604/378 |
| 2017/0258955 | A1 | 9/2017 | Lindner et al. |

FOREIGN PATENT DOCUMENTS

| | | |
|---|---|---|
| EP | 2266514 A1 | 12/2010 |
| EP | 2411061 B1 | 11/2014 |
| FR | 2789690 A1 | 8/2000 |
| GB | 1225824 A | 3/1971 |
| GB | 200205029 | 4/2002 |
| JP | 62129054 | 6/1987 |
| JP | 62133164 | 6/1987 |
| JP | 62268861 | 11/1987 |
| JP | 1272861 | 10/1989 |
| JP | 2191759 | 7/1990 |
| JP | 3279452 | 12/1991 |
| JP | 4091224 | 3/1992 |
| JP | 4136251 | 5/1992 |
| JP | 5051818 | 3/1993 |
| JP | 6070954 | 3/1994 |
| JP | 6245952 | 9/1994 |
| JP | 7258964 | 10/1995 |

(56) References Cited

FOREIGN PATENT DOCUMENTS

| | | |
|---|---|---|
| JP | 8158229 | 6/1996 |
| JP | 9049160 | 2/1997 |
| JP | 9111630 | 4/1997 |
| JP | 9273061 | 10/1997 |
| JP | 1025420 A1 | 1/1998 |
| JP | 2000178865 | 6/2000 |
| JP | 2002061060 | 2/2002 |
| JP | 2002263137 | 9/2002 |
| JP | 2003138428 | 5/2003 |
| JP | 2004169261 | 6/2004 |
| JP | 2004285538 | 10/2004 |
| JP | 2005330637 | 12/2005 |
| JP | 2007113145 | 5/2007 |
| JP | 2007154380 | 6/2007 |
| JP | 2008002037 | 1/2008 |
| JP | 2008095254 | 4/2008 |
| JP | 2008161584 | 7/2008 |
| JP | 200915005 | 7/2009 |
| JP | 2009228157 | 10/2009 |
| JP | 200301358 | 10/2013 |
| WO | WO1995023249 | 8/1995 |
| WO | WO1995023250 | 8/1995 |
| WO | WO1998008475 | 3/1998 |
| WO | WO1999006207 | 2/1999 |
| WO | WO1998031735 | 10/1999 |
| WO | WO2001090230 | 11/2001 |
| WO | 0209491 A2 | 2/2002 |
| WO | WO2002068746 A2 | 9/2002 |
| WO | WO2004014997 A2 | 2/2004 |
| WO | WO2005042824 | 5/2005 |
| WO | WO2007001270 A1 | 1/2007 |
| WO | WO2010149239 A1 | 12/2010 |
| WO | WO2011090425 A1 | 7/2011 |
| WO | WO2012162083 A1 | 11/2012 |
| WO | WO2012162085 A1 | 11/2012 |
| WO | WO2012162092 A1 | 11/2012 |
| WO | WO2012162130 A1 | 11/2012 |
| WO | WO2012162135 | 11/2012 |
| WO | WO2012162146 A1 | 11/2012 |
| WO | WO2012162149 A1 | 11/2012 |
| WO | WO2012162084 A3 | 3/2013 |

OTHER PUBLICATIONS

International Search Report and Written Opinion for PCT/US2018/021675 dated May 15, 2018.
Devesh, Tripathi, "Practical Guide to Polypropylene", Smithers RAPRA Technology, 2002.
Drexel University, Fiber Spinning—Drexel University Chemical Engineering Department, Feb. 16, 1999.
Flow Polymers Effect of SureFlo (TM) on Polypropylene Contamination in Nylon, 2011 Flow Polymers, LLC.
Kim, "Effects of Nucleating Agents on Preparation of Polypropylene Hollow Fiber Membranes by Melt Spinning Process", Maromolecular Research, vol. 10, No. 2, 127-134 pgs. (2002).
Kim, Microporous Membrane Formation Via Thermally Induced Phase Separation, Journal of Membrane Science, 64, (1991)13-29.
Kim, Operation Parameters of Melt Spinning of Polypropylene Hollow Fiber Membranes, Journal of Membrane Science 108 (1995) 25-36, 12 pages.
Krupa, Polypropylene as a Potential Matrix for the Creation of Shape Stabilized Phase Change Materials, European Polymer Journal 43 (2007) 895-907, 13 pages.
Krupa, Thermal Properties of Polypropylene/Wax Blends, Thermochimica Acta 372 (2001) 137-141, 5 pages.
Mpanza, Comparison of Different Waxes as Processing Agents for Low-Density Polyethylene, Polymer Testing 25 (2006) 436-442, 7 pages.
Tolinski, Additives for Polyolefins, 2009, pp. 158-168.
Xiaofan, Flow Polymers, Effects of SureFlo® on the Crystallization and Melting Behavior of Semi-Crystalline Polyethylene (PE) and Polypropylene (PP) Systems, Flow Polymers, LLC, 3 pages.
Yoo, Effects of the Diluent Mixing Ratio and Conditions of the Thermally Induced Phase-Separation Process on the Pore Size of Microporous Polyethylene Membranes, Journal of Applied Polymer Science, vol. 108, 3154-3162 (2008).
All Office Actions for U.S. Appl. No. 15/454,128, filed Mar. 9, 2017.

\* cited by examiner

THERMOPLASTIC POLYMERIC MATERIALS WITH HEAT ACTIVATABLE COMPOSITIONS

FIELD OF THE INVENTION

The disclosure herein relates generally to thermoplastic polymeric materials with heat activatable melt additives.

BACKGROUND OF THE INVENTION

Nonwovens and films have been used in a myriad of absorbent articles over the past several years. In some particular absorbent articles, e.g. diapers and feminine hygiene pads, nonwovens and/or films may be utilized as a topsheet, backsheet, or some other feature of these particular absorbent articles.

The requirements for these absorbent articles may be disparate depending use. For example, a nonwoven and/or film used as a topsheet for diapers may not be suitable for adult incontinence products. Similarly, a nonwoven and/or film suitable as a topsheet for adult incontinence products may not be suitable for feminine hygiene pads.

Additionally, requirements for nonwoven and/or films in absorbent articles may vary by location. For example, in one location an absorbent article with a soft topsheet may be a factor which is foremost in consumer's minds. In another location, absorbent articles which minimize the amount of rewet may be foremost in consumer's minds. In yet another location, the speed of acquisition of liquid insults may be foremost in consumer's minds. In yet another location, the amount of masking provided by a topsheet may be foremost in consumer's minds.

It would be beneficial for a nonwoven web to address one or more of the above concerns and allow for the flexibility of addressing multiple of the above concerns. It would also be beneficial to have a process which facilitated the production of nonwoven webs capable of addressing one or more of the above concerns and to provide a process providing the flexibility to address multiple of the above concerns.

SUMMARY OF THE INVENTION

Disclosed herein are permeable material webs with modified tactile properties and/or hydrophilic melt additives which can be used in absorbent articles including disposable absorbent articles. Some exemplary uses of permeable material webs include a topsheet, a secondary topsheet, an acquisition layer or distribution layer of an absorbent article. The material webs of the present disclosure, when utilized as an acquisition layer of a feminine hygiene article or diaper, can provide can provide quick acquisition of menses/urine insults. Some exemplary uses of permeable material webs with modified tactile properties include a backsheet nonwoven, which can be further laminated to film, a front ear nonwoven and/or a backear nonwoven. Other benefits and configurations are discussed hereinafter.

The material webs of the present invention may be heated treated to promote the blooming of a melt additive blended with the constituent material of the material web. And, depending on the type of heat treatment and/or time thereof, as disclosed herein, properties of the material webs may be altered from location to location as desired which can allow for much flexibility with the use of the material webs described herein. Nonwoven webs which are treated with melt additives for the purposes of creating a fluid barrier are excluded from the material webs of the present disclosure.

In some forms, a permeable nonwoven web comprises a first surface and a second surface with a thickness defined by the first surface and the second surface. The nonwoven web further comprises: a plurality of fibers and/or filaments, wherein each of the plurality of fibers and/or filaments comprise a first constituent polymer matrix which forms an outer surface of each of the fibers and/or filaments, and wherein the first constituent polymer matrix comprises a hydrophilic melt additive and/or a tactile modifying melt additive, and wherein the hydrophilic melt additive and/or tactile modifying melt additive blooming is present on the outer surface of the fiber and/or filaments at least at one of the following areas: at a plurality of junctions between the fibers and/or filaments; at a plurality of localized areas through the thickness of the nonwoven web; or through the thickness of the entire nonwoven web.

In some forms, a permeable nonwoven web has a first surface and an opposing second surface, and a thickness defined by the first surface and the second surface. The permeable nonwoven web further comprises: a plurality of bi-component staple fibers, each of the plurality of bi-component staple fibers being arranged in a core-sheath arrangement, the sheath comprising a first constituent polymer matrix and the core comprising a second constituent polymer matrix, wherein a melting temperature of the second constituent polymer matrix is between 20 degrees C. to 50 degrees C. higher than a melting temperature of the first constituent polymer matrix; a hydrophilic and/or tactile modifying melt additive blended with the first constituent polymer matrix; and a plurality of bloom areas disposed through the thickness of the permeable nonwoven web, the plurality of bloom areas being disposed on an outer surface of the sheath.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

DETAILED DESCRIPTION OF THE INVENTION

Figure 1:
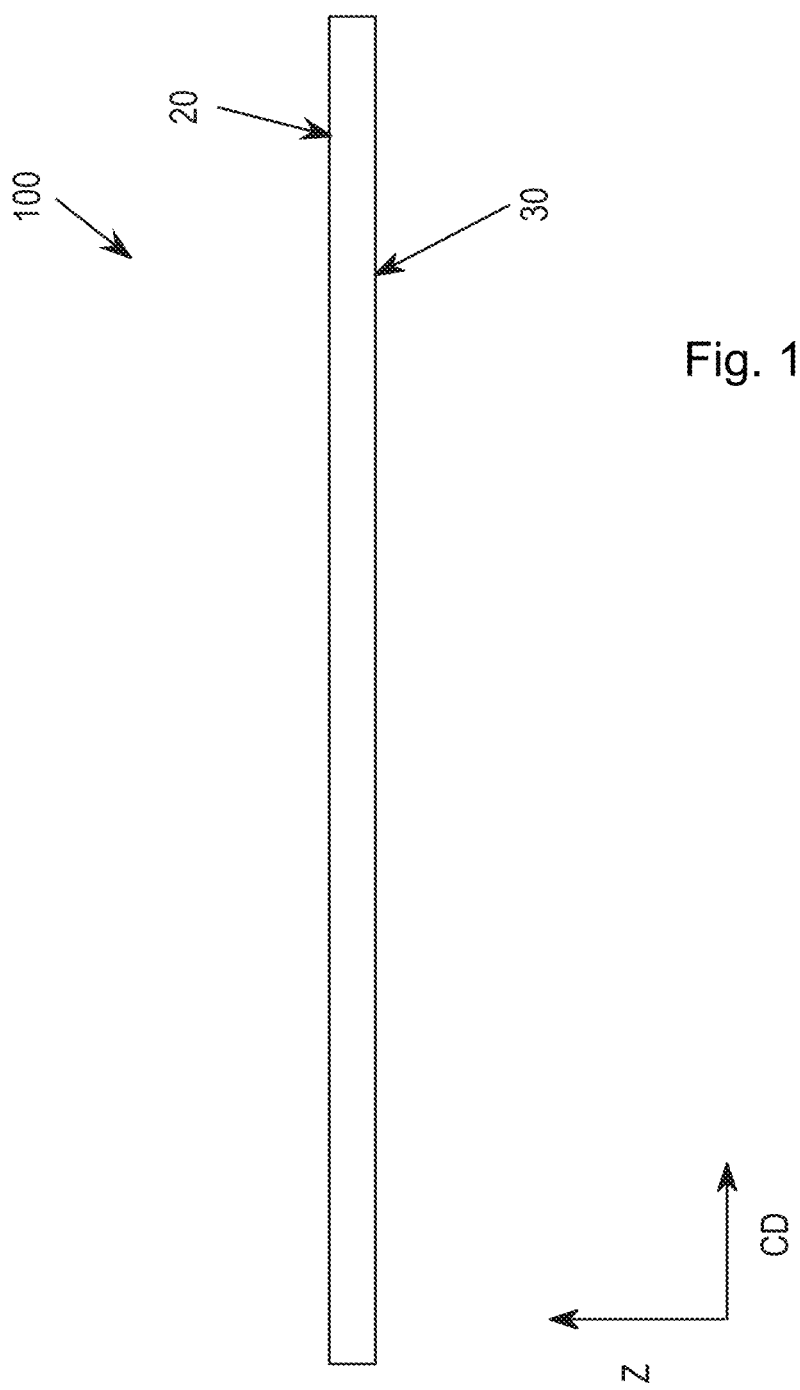
FIG. 1 is a schematic representation of a cross section of a material web of the present invention.

As used herein "disposable absorbent article" or "absorbent article" shall be used in reference to articles such as diapers, training pants, diaper pants, refastenable pants, adult incontinence pads, adult incontinence pants, feminine hygiene pads, tampons, and pessary devices.

As used herein "hydrophilic" and "hydrophobic" have meanings well established in the art with respect to the contact angle of a referenced liquid on the surface of a material relative to the art. Thus, a material having a liquid contact angle of greater than about 90 degrees is generally considered hydrophobic, and a material having a liquid contact angle of less than about 90 degrees is generally considered hydrophilic. Compositions which are hydrophobic, will increase the contact angle of a referenced liquid on the surface of a material while compositions which are hydrophilic will decrease the contact angle of a referenced liquid on the surface of a material. Notwithstanding the foregoing, reference to relative hydrophobicity or hydrophilicity between material(s) and/or composition(s) does not imply that the material or composition are hydrophobic or hydrophilic. For example, a composition may be more hydrophobic than a material. In such a case neither the composition nor the material may be hydrophobic; however, the contact angle of water droplets on the composition is greater than that of water droplets on the material. As another example, a composition may be more hydrophilic than a material. In such a case, neither the composition nor the material may be hydrophilic; however, the contact angle with respect to water droplets exhibited by the composition may be less than that exhibited by the material. In general, materials which demonstrate a high surface energy may be considered to be more hydrophilic than materials which have a low surface energy.

As used herein, "spunbond filaments" refers to small diameter filaments which are formed by extruding molten thermoplastic material as filaments from a plurality of fine capillaries of a spinneret with the diameter of the extruded filaments then being rapidly reduced. Spunbond filaments are generally not tacky when they are deposited on a collecting surface. Spunbond filaments are generally continuous and have average diameters (from a sample of at least 10) larger than 7 microns, and more particularly, between about 8 and 40 microns.

The term "filament" refers to any type of artificial continuous strand produced through a spinning process, a meltblowing process, a melt fibrillation or film fibrillation process, or an electrospinning production process, or any other suitable process to make filaments. The term "continuous" within the context of filaments are distinguishable from staple length fibers in that staple length fibers are cut to a specific target length. In contrast, "continuous filaments" are not cut to a predetermined length, instead, they can break at random lengths but are usually much longer than staple length fibers.

By "substantially randomly oriented" it is meant that, due to processing conditions of a nonwoven web, there may be a higher amount of filaments oriented in the machine direction (MD) than the cross direction (CD), or vice-versa.

The material webs of the present invention may comprise a nonwoven, or a laminate created therefrom, e.g. a nonwoven/nonwoven laminate, film/nonwoven laminate, or film/nonwoven composite. Additionally, the material webs of the present invention may comprise any suitable nonwoven. Some exemplary nonwovens are discussed in additional detail in the section entitled, "Precursor Material."

Referring to FIG. 1, material webs 100 of the present disclosure comprises a first surface 20 and an opposing second surface 30 defining a thickness therebetween. The material webs 100 of the present invention have a machine direction (MD) (perpendicular to the plane of the sheet showing FIG. 1), a cross machine direction (CD), and the Z-direction, as is commonly known in the art of web manufacture.

The material web 100 of the present disclosure comprises a constituent material—typically a thermoplastic polymer sometimes referred to as a "polymer matrix." In addition to the polymer matrix, the constituent material additionally comprises a melt additive. For example, in the case of nonwoven materials, the fibers and/or continuous filaments of the material web 100 may comprise a hydrophilic melt additive or a tactile modifying agent. Suitable hydrophilic melt additives and tactile modifying agents are discussed hereafter.

The melt additive may be blended with the thermoplastic polymeric material of the filament and/or fibers. In the case of bi-component or multi-component fibers and/or filaments, the melt additive may be blended with a component of the bi-component or multi-component fiber and/or filament but not necessarily across the entirety of the fiber or filament. For example, a fiber and/or filament having a core-sheath configuration may comprise a melt additive blended with the polymer matrix of the sheath, while the core does not comprise the melt additive of the sheath. Or, the core may comprise the melt additive of the sheath, but in a different amount than that of the sheath. Or, in some forms, the polymer matrix of the core may comprise the same melt additive of the sheath but in a greater amount. Or in other forms, the polymer matrix of the core may comprise the melt additive of the sheath and in the same weight percentage as the sheath.

The inventors have surprisingly found that with the application of energy, e.g. thermal energy, melt additive blooming can be facilitated. For example, thermal energy can be applied to the entirety of the material web 100 to facilitate the melt additive blooming across the first surface and/or second surface of the material web 100 and/or throughout the thickness of the material web 100 in the Z-direction. This can provide the ability to raise or lower the surface energy of the material web 100 where normal processing, e.g. coating, would not be feasible. For example, where the material web 100 comprises multiple strata (discussed hereafter), post treatment of the material web 100, via thermal energy application, may impact the entirety of the material web 100 throughout its thickness rather than a desired stratum in the case of a coating which may not be desirable.

As noted previously, the amount of melt additive which blooms in the material web can increase with the application of energy, e.g. thermal energy. In some forms, thermal energy may be applied uniformly across the material web 100. In other forms, heat may be applied in one or more discrete areas of the material web 100. Accordingly, the material webs may be rendered more hydrophilic than what would otherwise be the case sans the heat treatment of the material web. This allows for much versatility of the use of the material web.

For the application of thermal energy across the entirety of the material web, any suitable method of thermal energy application may be utilized. Some examples include the use of microwave (radio frequency) radiation. This approach is particularly powerful if a salt solution (e.g. potassium acetate in poly ethylene glycol) has been sprayed onto the surface of the material web. The radiation will then let the ions of the salt vibrate, which causes friction, which causes heat. Ultrasonic heating may also be used.

In some forms, material webs of the present invention may be air through bonded. Such bonding is achieved via heat application over the entire web. This application of heat can achieve blooming as described herein without the additional provision of heat during subsequent processing. Additionally, as carded webs comprise staple fibers, the blooming effect described herein may be enhanced. For example, in typical staple fiber making, heat is provided during drawing and drying steps, e.g. 100 degrees C. for a minimum of 1 minute. And, during air through bonding, the web may be exposed to heat of about 130 to about 160 degrees C. for a period of about 3 to 5 seconds and depending on the line speed up to 10 seconds.

Given the additional processing required by staple fiber material webs, air through bonding may not be required to promote melt additive blooming. For example, forms are contemplated where a staple fiber material web is hydroentangled post the drawing and drying steps. In some forms, the staple fiber web may be calendar bonded post the drawing and drying steps. In some forms, the staple fiber web may be air through bonded.

For some forms of staple fibers and/or filaments, the melt blooming effect can be enhanced. For example, for staple fibers and/or filaments that are bi-component, e.g. core/sheath, the melt additive can be provided in the sheath only. In such forms, the melt additive may have a shorter diffusion length which can enhance the melt additive blooming effect with applied thermal energy. One specific example of this form, is where the core comprises polyethylene terephthalate and the sheath comprises co-polyethylene terephthalate or polyethylene. A hydrophilic melt additive may be provided in the sheath. A nonwoven material comprising these staple fibers and/or filaments may be air through bonded thereby promoting blooming of the hydrophilic melt additive to the surface of the staple fibers and/or filaments. And because the hydrophilic melt additive is only available in the sheath, the melt additive has a much shorter diffusion distance than if a mono-component filament and/or fiber. This nonwoven may then be utilized as an acquisition layer and/or distribution layer to remove liquid insults from a topsheet of a disposable absorbent article.

And, combining both on-line heating and tempering can synergistically increase the effect. An optimized thermal energy application step (highly effective in line heat insertion, e.g. via IR dryer) can be translated into further usage reduction and/or better performance.

The heat application of the aforementioned processes may be applied as part of the making process, directly after spinning of the fibers and/or filaments and laydown of the web—as part of the bonding process (via a heated calendar) or a subsequent step (e.g. drum dryer or, most effectively, infrared heater). In this case typically high temperatures can be applied. An exposure in the seconds or even mili seconds range may be sufficient depending on the constituent material of the material web. Additionally, the amount of thermal energy required to promote melt additive blooming depends on whether the application of thermal energy is performed within a short period of time after formation of the material web. For material webs which are subjected to thermal energy application immediately subsequent to production, a lower amount of thermal energy may be required to promote melt additive blooming as opposed to material webs which were not subjected to thermal energy application subsequent to formation.

Alternatively, the heat activation can be done via tempering of the final material web over several days, e.g. 3 to 7 days. For example, it has been found that for permeable material webs with modified tactile properties comprising a glycerol tristearate Masterbatch that the temperature window for such tempering can be between about 30 degrees C. to less than about 52° C. (as of 52° C. the glycerol tristearate fibrils will melt again) or from between about 32° C. to about 50° C., or from between about 37° C. to about 45° C., specifically including all values within these ranges and any ranges created thereby. In some forms, a temperature of 37° C. may be utilized. Tempering can be done with fresh samples (not more than a few hours after making). Older samples may require additional thermal energy input.

The inventors have found that effective blooming may be achieved by tempering a material web as described herein for at least 1 day, or for 3 to 4 days, or for 5 to 7 days. While tempering for longer periods of time, e.g. 30 days, may be performed, the amount of additional blooming achieved after 7 days may be considerably less than what is bloomed during the 7 day tempering period. Additionally, a shorter tempering time is also advantageous from a manufacturing practicality point of view.

It has been found generally and across a variety of melt additives tested that blooming via tempering can be increased if the tempering of the final material web is done at a temperature which is slightly below the onset of melting of the melt additive. For example, a tempering temperature of 10° C. to 15° C. lower than the onset temperature of melting of the melt additive but no less than 5° C. and no more than 20° C. below the onset temperature of melting of the melt additive can achieve good blooming results. The onset temperature of melting is determined via Differential Scanning Calorimetry (DSC) and is defined as the intersection of the left tangent of the DSC melting peak with the extrapolated baseline.

It has also been found that tempering of the final material web at a temperature above the onset of melting of the melt additive does not lead to further enhanced blooming, but instead, may cause the already bloomed melt additive to migrate back from the surface into the polymer matrix. If the tempering is done at a temperature corresponding to the minimum of the melting peak, it has been found that the treatment will result in no blooming at all. Without wanting to be bound by theory, it is believed that the preferred temperature window(s) for tempering, as described herein, provide an increased diffusion coefficient enabling faster blooming while maintaining a sufficient incompatibility between melt additive and polymer, which is the driving force for blooming. Higher tempering temperatures can increase the diffusion coefficient; however, higher tempering temperatures can also lower the incompatibility between the melt additive and the polymer matrix which can discourage blooming. It is believed that the polymer melt additive systems described in the present invention are Upper Critical Solution Temperature systems, which show decreasing incompatibility with increasing temperature.

As an example, for the hydrophilic melt additive Brij S2 from Croda in polypropylene (grade: Moplen HP561R), best blooming results were achieved via tempering at 30° C. for 3 days, whilst tempering at 40° C. resulted in significantly worse blooming results compared to the 30° C. treatment. Tempering at 50° C. resulted in no blooming at all. Brij S2 has an onset of melting at 43° C. and a peak temperature of 47° C. For Brij S100 from Croda, in contrast, which is a longer molecule (containing 100 instead of 2 ethylene oxide repeat units) with accordingly lower diffusion coefficient and which has an onset of melting of ~50° C., best blooming results were achieved via tempering at a temperature of 40° C. while nearly no blooming happened when the filaments were left at 20° C.

It has also been found that polymer melt additive blends whose DSC curve shows a distinct separate melting peak for melt additive are particularly effective in blooming. That separate peak associated with the melt additive is at a temperature which is very close to the melting temperature of the pure melt additives, typically about 5° C. lower. It is believed that the presence of that separate peak is an indicator of the required "sufficient incompatibility" between melt additive and polymer.

An additional advantage of the material webs of the present invention is that conventional acquisition layers may require latex bond agents to provide binding among the fibers of the acquisition layers. And, the acquisition layers are often hydrophilic because of the latex binder. While these latex binders typically do not lose hydrophilicity over time, they tend to release odorous components over time which some users can find offensive or repulsive.

In contrast, the air through bonded carded nonwoven webs of the present disclosure do not require latex binder as the air through bonding provides the nonwoven web with structural integrity. As such, air through bonded nonwoven webs of the present disclosure are substantially latex free which means that the air through bonded nonwoven web of the present disclosure comprise less than 1 percent by weight of latex. As such, the air through bonded carded nonwoven webs do not release the odorous components associated with latex binders. Additionally, the air through bonded carded nonwoven webs of the present invention tend to be softer than their latex bonded counterparts.

The melt additive may form between about 0.1 percent by weight to about 10 percent by weight of the material web 100. In some forms, the melt additives may be less than about 10 percent by weight, less, less than about 8 percent by weight, less than about 6 percent by weight, less than about 5 percent by weight, less than about 3 percent by weight, less than about 2.5 percent by weight, or less than about 1 percent by weight, specifically including any values within these ranges or any ranges created thereby. In some forms, the melt additive may be about 6 percent by weight of a master batch containing 40 percent by weight of the melt additive. In some forms, the melt additive may form between about 0.5 percent by weight to about 6 percent by weight of the master batch or from about less than 4 percent by weight of the master batch or any value within these ranges and any ranges created thereby.

Regarding localized blooming, the inventors have found that if the concentration of melt additive by weight percent is too low, the melt additive bloom areas provided with localized heat application may not be sufficient to provide the desired functionality. In contrast, if the melt additive concentration is too high, melt additive bloom areas may occur without the localized heat application—auto blooming. Without wishing to be bound by theory, it is believed that the amount of diffusion, e.g. diffusion coefficient (explained in additional detail below), of the melt additive increases with the concentration of melt additive in the polymer matrix of the constituent material of the material web.

In some forms of the present invention localized blooming may be promoted through the application of energy to a material web, e.g. by use of a hot air knife, or a belt with apertures of defined geometry through which hot air is inserted into the material web, or via IR irradiation using a template light patterns, or via laser marking (e.g. as used in the production of packaging materials). Additional suitable methods for the application of localized energy to a material web are described in U.S. Patent Application Publication No. 2017/0258955.

As described above for heating of the entire web, with localized (zoned) blooming, blooming across the z-direction (thickness) of the web in the zones where the heat is applied can be achieved. In some forms, the blooming may be homogeneous in the z-direction. In contrast, topical coatings may only impact a portion of the thickness, e.g. top or bottom, of the material web rather than be present throughout the thickness of the material web, at least shortly after application. Additionally, post application of topical coatings, they can have a tendency to migrate laterally across the surface of the material to which they are applied as well as in the Z-direction into the thickness of the material web. Lateral migration of the topical coating can detrimentally impact the desire to have discrete treated areas. Migration of coating in the lateral direction as well as the Z-direction is discussed in additional detail herein.

In contrast to topical coatings, melt additives can be selected in a way that discourages lateral migration over time across the surface. Suitable melt additives and their selection criteria are discussed hereafter. Without wishing to be bound by theory, it is believed that the glass transition temperature of the polymer which makes up the material of the web, the molecular weight of the melt additive, as well as the chain length of the melt additive, the incompatibility of the melt additive and polymer at the temperature at which blooming is to happen can impact the blooming capability of the melt additive. It is believed that where the polymer is in its glassy state, the glassy state of the polymer matrix can "lock away" the melt additive and discourage blooming. It was e.g. observed that melt additives which bloom out of poly propylene at room temperature do not bloom at all when the sample is stored right after making at a temperature of minus 12° C., i.e. below the Tg of PP (~5° C.). In order to promote blooming of the melt additive from a polymer which is in its glassy state, i.e. its Tg is above the ambient temperature, the polymer needs to be heated above its Tg.

For those polymers which comprise a high Tg, e.g. polystyrene 100 degrees C.; polycarbonate 145 degrees C.; polylactic acid 60 to 65 degrees C.; polybutylene terephthalate (69 to 85° C.), the melt additives that can be utilized for zoned blooming may be more extensive than for those polymers with lower glass transition temperatures. In zone (localized) blooming, "blooming" or "not blooming" may be controlled by the temperature of the zone. In zones with T>Tg, blooming is possible while in zones with T<Tg no blooming or reduced blooming may occur. For those polymers with lower Tg's, e.g. polypropylene, polyethylene, the melt additives which can be utilized for zoned blooming are limited to some extent, particularly where zoned blooming is desired. With lower Tg's of the constituent material, some melt additives may auto bloom at room temperature, e.g. about 25 degrees C. Where auto blooming is not desired, glass transition temperatures of the thermoplastic polymeric materials are preferably greater than room temperature. This selection will discourage auto blooming and instead allow for zoned blooming via local energy application. In some forms, in the case of a sheath-core bi-component filament or fiber, the core component may have a glass transition temperature which is greater than room temperature.

For those polymers with a high Tg, any suitable hydrophilic additive can be used. Some suitable examples include those available from Techmer PM, Clinton, Tenn. sold under the trade name of Techmer PPM15560; TPM12713, PPM19913, PPM 19441, PPM19914, PPM11029, and PM19668. Additional examples are available from Polyvel Inc. located in Hammonton, N.J., sold under the trade name of Polyvel VW351 PP Wetting Agent; from Goulston Technologies Inc. located in Monroe, N.C. sold under the trade name Hydrosorb 1001; as well as those hydrophilic additives disclosed in US Patent Application Publication No. 2012/0077886 and U.S. Pat. Nos. 5,969,026 and 4,578,414. Other suitable hydrophilic melt additives are Unithox 720, Unithox 750, available from Baker Hughes and Techsurf 15560 from Techmer in general. Additionally, Techmer PBM19276 can be used for polybutylene terephthalate or CoPolyethyleneterephtahlate.

For those polymers with a lower glass transition temperature, e.g. polypropylene 5 degrees C. (uninfluenced domains), polyethylene minus 125 degrees C., the list of available melt additives may be much more restrictive for zoned blooming via local activation—assuming that the desired outcome is to discourage auto blooming. Without wishing to be bound by theory, it is believed that for those polymers with a lower Tg, the chain length and molecular weight of the melt additives become much more critical in whether auto blooming will occur. It is believed that for those melt additive compositions having a higher chain-length and a higher molecular weight, a lower diffusion coefficient in the polymer exists at room temperature. So, it is believed that for higher chain length melt additive compositions, auto blooming will be discouraged at room temperature.

Where auto blooming is desired to be encouraged, polymers with a low glass transition temperature may be coupled with any suitable hydrophilic melt additive or any tactile modifying melt additive. Specifically, those melt additives listed for use with the polymers having a higher glass transition temperature may be utilized in conjunction with low glass transition temperature polymers where auto blooming is desired.

However, where auto blooming is not desired, an exemplary hydrophilic melt additive which can be utilized in combination with polypropylene and/or polyethylene is Polyvel surfactant S-1416. It is believed that homologues with a higher molecular weight than Polyvel surfactant S-1416 in a polypropylene or polyethylene matrix may also be utilized. Another suitable melt additive for polyethylene is sorbitan monolaureate.

The Polyvel S-1416 is a silicon surfactant with a (hydrophilic) poly ethylene oxide (PEO) chain and molecular weight above 700 g/mol. Polyvel S-1416 is available from Polyvel Inc. and is also known under the trade name "VW 351." Without wishing to be bound by theory, it is believed that the "resistance to blooming" is controlled via the length of the PEO chain. Namely, it is believed that the longer the PEO chain, the larger the resistance to blooming. S-1416 has a chain of 10 or 11 ethylene oxide repeat units. Additionally, activation of S-1416 requires besides heating a humid environment (e.g. 80% relative humidity or in the presence of water sprayed onto the surface). It further believed that under these conditions the hydrophilic tail is flipped outward.

In air through bonded webs, increased local blooming of a suitable melt additive can be also achieved at the bonding points, i.e. the junctions between individual fibers and/or filaments, i.e. where the fibers and/or filaments touch each other, and are thermally welded into each other. This can be achieved even if the entire web is uniformly treated with heat, when a melt additive-polymer combination with discouraged auto-blooming is used, e.g. Polyvel S-1416 in polypropylene. Without wanting to be bound by theory, it is believed that the increased melt flow of the polymer, which happens at the bonding points, generates additional convection in the molten polymer which supports blooming.

It is believed that local hydrophilicity at junction points: enables a macroscopically hydrophobic structure (good for dryness, particularly if used as topsheet nonwoven) but hydrophilic connection points still enable liquids to pass through nonwoven web. The hydrophilic connection points may be particularly advantageous for "super-thin" fibers and/or filaments (<1.5 dpf) (e.g. better softness due to lower bending modulus) which are particularly difficult to keep dry they are hydrophilic.

One of the advantages of utilizing a hydrophilic melt additive over topical coatings is that material webs with hydrophilic coatings can lose their hydrophilicity over time. As mentioned previously, it is believed that there are two primary mechanisms which can negatively impact hydrophilic coatings over time. First, it is believed that the topical coating can vertically diffuse from the surface into the polymer matrix of the nonwoven web after application. Such migration can mean a loss of hydrophilicity where the coating was initially applied. This can negatively impact fluid handling performance. Second, as noted previously, it is also believed that the topical coating can laterally migrate over the surface of the material web which can cause contamination of other parts of the hygiene products.

Some hydrophilic melt additives can avoid these issues though. It is further believed that the avoidance or reduction of such issues with melt additives is due, at least in part, to the incompatibility of the melt additive with the polymer matrix. It is additionally believed that such issues with melt additives can be avoided or reduced because the hydrophobic parts (longer chain tails) of the melt additive are believed to be anchored in the polymer and only the hydrophilic head of the melt additive molecule is above the surface of the polymer. The longer the hydrophobic chain, the stronger the anchoring effect and the better the resistance to aging, but the slower the diffusion to the surface. This limitation of slower diffusion can be overcome by heat application which increases the diffusion coefficient of the melt additive.

Even when melt additives are used, instead of topical coatings, and the above two issues are avoided, there is still a further aging mechanism, which specifically applies for multiple component fibers, in which the melt additive is used only in the one component, e.g. in the sheath. In some cases, the melt additive can diffuse over time from the component comprising the melt additive into the component comprising no melt additive or less of the melt additives, which is typically the core. As a consequence, the amount of melt additive available for blooming in the sheath is reduced. Without wanting to be bound by theory, it is believed that the core can act as a "thermodynamic sink" which is able to take up parts of the melt additive. In such instances, the concentration gradient between core and sheath can be the driving force for diffusion of melt additive from the sheath into the core, and in the newly established thermodynamic equilibrium, a lower amount of melt additive is present in the sheath.

In contrast, selection of the fiber and/or filament materials as described herein can reduce the likelihood of the core becoming a thermodynamic sink. For example, by using a polymer with a sufficiently high glass transition temperature in the core (respectively in the component of the fiber that is supposed to contain no or a reduced amount of melt additive) this problem can be alleviated. The glass transition temperature of the core, or the component to which migration of a melt additive is not desired, should be at least larger than 25° C., and or in some forms, larger than 40° C. It is believed that a polymer in its glassy state is largely inaccessible to the penetration of a melt additive, for the same reasons of kinetic hindrance as discussed above in the context of polymer-melt additive combinations for zoned blooming.

For applications of blooming of a hydrophilic melt additive, e.g. from the sheath of a bicomponent fiber as used in an airthrough bonded web, the following polymer melt additive combinations were found well suited:

For polyethylene, PM 19668 from Techmer (hydrophilic PE masterbatch) or, preferably, Atmer 7326 available from Croda (Croda PE Antifog masterbatch), or also Brij S2 from Croda (available as pure substance), can be used. The typical dosage for PM 19668 is between 0.5 and 2 weight percent of the masterbatch. The typical dosage of Atmer 7326 is 5 weight percent of the masterbatch and Brij S2 is 1 to 3 weight percent, preferably 2 weight percent, of the active.

For polypropylene, PPM 15560 from Techmer (hydrophilic PP masterbatch) or Brij S2 can be used most preferably. Further, in order of declining preference, Bij S10 (from Croda,) Unithox 450, Unithox 720 and Unithox 750 (from Baker Hughes) can be used. PPM 15560 is preferably used in a dosage of 0.5 weight percent of the masterbatch, Brij S2 and Brij S10 in a dosage of preferably 2 weight percent of the active. The Unithox melt additives require additional tempering.

For co(polyethylene terephthalate): Techmer PBM19276.

In addition to the melt additives described heretofore, or independently thereof, additional melt additives may be provided in the polymer matrix of a material web. For example, suitable tactile melt additives can be a hydrocarbon having one or more functional groups selected from hydroxide, aryls and substituted aryls, halogens, alkoxys, carboxylates, esters, carbon unsaturation, acrylates, oxygen, nitrogen, carboxyl, sulfate and phosphate. In one particular form, the slip agent is a salt derivative of an aromatic or aliphatic hydrocarbon oil, notably metal salts of fatty acids, including metal salts of carboxylic, sulfuric, and phosphoric aliphatic saturated or unsaturated acid having a chain length of 7 to 26 carbon atoms, or from 10 to 22 carbon atoms. Any fatty acid amide melt additive that can reduce the coefficient of friction of the material web may be utilized. Suitable fatty acid amides include those derives from a mixture of C12-C28 fatty acids (saturated or unsaturated) and primary or secondary amines. A suitable example of a primary fatty acid amide includes those derived from a fatty acid and ammonia as illustrated in [1].

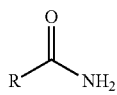

where R has a number of carbon atoms ranging from 11 to 27, in particular from 16 to 22 fatty acid.

In other forms, the tactile agent is a non-ionic functionalized compound. Suitable functionalized compounds include: (a) esters, amides, alcohols and acids of oils including aromatic or aliphatic hydrocarbon oils, for example, mineral oils, naphthenic oils, paraffinic oils; natural oils such as castor, corn, cottonseed, olive, rapeseed, soybean, sunflower, other vegetable and animal oils, and so on. Representative functionalized derivatives of these oils include, for example, polyol esters of monocarboxylic acids such as glycerol monostearate, glycerol tristearate, pentaerythritol monooleate, and the like, saturated and unsaturated fatty acid amides or ethylenebis(amides), such as oleamide, erucamide, linoleamide, and mixtures thereof, glycols, polyether polyols like Carbowax, and adipic acid, sebacic acid, and the like; (b) waxes, such as carnauba wax, microcrystalline wax, polyolefin waxes, for example polyethylene waxes; (c) fluoro-containing polymers such as polytetrafluoroethylene, fluorine oils, fluorine waxes and so forth; and (d) silicon compounds such as silanes and silicone polymers, including silicone oils, polydimethylsiloxane, amino-modified polydimethylsiloxane, and so on.

The fatty amides useful in the present invention are represented by the formula: $RC(O)NHR^1$ where R is a saturated or unsaturated alkyl group having of from 7 to 26 carbon atoms, or from 10 to 22 carbon atoms, and $R^1$ is independently hydrogen or a saturated or unsaturated alkyl group having from 7 to 26 carbon atoms, or from 10 to 22 carbon atoms. Compounds according to this structure include for example, palmitamide, stearamide, arachidamide, behenamide, oleamide, erucamide, linoleamide, stearyl stearamide, palmityl palmitamide, stearyl arachidamide and mixtures thereof.

The ethylenebis(amides) useful in the present invention are represented by the formula:

$$RC(O)NHCH_2CH_2NHC(O)R$$

where each R is independently is a saturated or unsaturated alkyl group having of from 7 to 26 carbon atoms, or from 10 to 22 carbon atoms. Compounds according to this structure include for example, stearamid.oethylstearamide, stearamidoethylpalmitamide, palmitamidoethylstearamide, ethylenebisstearamide, ethylenebisoleamide, stearylerucamide, erucamidoethylerucamide, oleamidoethyloleamide, erucamidoethyloleamide, oleamidoethylerucamide, stearamidoethylerucamide, erucamidoethylpalmitamide, palmitamidoethyloleamide and mixtures thereof.

Commercially available examples of fatty amides include Ampa et 10061 which comprises 5 percent of a 50:50 mixture of the primary amides of erucic and stearic acids in polyethylene; Elvax 3170 which comprises a similar blend of the amides of erucic and stearic acids in a blend of 18 percent vinyl acetate resin and 82 percent polyethylene. These slip agents are available from DuPont. Slip agents also are available from Croda Universal, including Crodamide OR (an oleamide), Crodamide SR (a stearamide), Crodamide ER (an erucamide), and Crodamide BR (a behenamide); and from Crompton, including Kemamide S (a stearamide), Kemamide B (a behenamide), Kemamide O (an oleamide), Kemamide E (an erucamide), and Kemamide (an N,N'-ethylenebisstearamide). Other commercially available slip agents include Erucamid ER erucamide.

Other suitable melt additives for softness/reduction of the coefficient of friction include erucamide, stearamide, oleamide, and silicones e.g. polydimethylsiloxane. Some specific examples include Crodamide™ slip & anti-block agents from Croda™, and Slip BOPP from Ampacet™. Some additional specific examples of softness/reduction of the coefficient of friction melt additives specifically tailored for polypropylene are from Techmer™ and sold under the trade names, PPM16368, PPM16141, PPM11790, PPM15710, PPM111767, PPM111771, and PPM12484. Some specific examples specifically tailored for polyethylene are from Techmer™ and sold under the trade name PM111765, PM111770, and PM111768.

Surprisingly it has been found that the hydrophilic melt additive Brij S2 has also a tactile modifying effect, rendering fibers softer. This effect can be enhanced by increasing the dosage beyond 2 weight percent of the active, as found favorable for its application as hydrophilic melt additive. Also surprisingly it has been found that even at high dosages, up to 10 or even 20 weight percent, no problems have been observed in the spinning process, like spinning instabilities which frequently occur if other melt additives are used in comparable dosages.

Air through bonded webs were found particularly advantageous to make use of any tactile/softness benefit which is provided by melt additives. Unlike their calendar bonded counterparts, air through bonded webs do not comprise bonding points having a plastic like, "non-textile" nature with lower bending flexibility. Such bonding points were found to diminish the enhanced softness/tactile impression of the material web.

As mentioned previously, for those forms of the present invention where auto-blooming is desired, then the melt additive list provided with regard to the higher Tg polymers may be utilized in conjunction with polymers having a lower Tg, e.g. polypropylene and/or polyethylene. And, in such instances, the application of heat to the material web as described herein can enhance the blooming of the melt additive, namely increasing the amount of melt additive which blooms to the surface. In contrast, where the discouragement of auto blooming is desired, the melt additive and the thermoplastic polymeric material may be matched as described herein such that auto blooming is discouraged. Note that the discouragement of auto blooming does not necessarily mean that auto blooming is precluded.

As discussed previously, the inventors have surprisingly found that the melt additive bloom areas do not laterally migrate to the same extent as topically applied compositions. This is advantageous to avoid loss of functionality via aging with the web losing its hydrophilicity or tactile properties and other parts of the absorbent article being contaminated (e.g. barrier layers like the barrier leg cuffs becoming hydrophilic due to lateral migration of a hydrophilic melt additive which makes them more permeable to body liquids). Without wishing to be bound by theory, it is believed that the glass transition temperature of the melt additive composition or the melt temperature of the melt additive (whichever is higher) needs to be above 25° C. or in some forms, above 40 degrees C. Higher melt temperatures or glass transition temperatures of the melt additives are believed to inhibit lateral migration of the melt additive.

Additionally, it believed that the diffusion coefficient plays an important part of whether a melt additive blooms. The melt additive diffusion coefficient can be defined as:

$$D_{\mathit{eff}} = \frac{x^2}{2t}$$

where Deff is the diffusion coefficient, x=radius of the fiber or half caliper of the film, and t=storage time. In order for the melt additive to stay within the polymer matrix of the material web (no melt additive bloom areas sans the application of thermal energy), the diffusion coefficient needs to fulfill the condition:

$$D_{\mathit{eff}} < \frac{x^2}{6 \text{ years}}$$

at room temperature or $$D_{\mathit{eff}} < \frac{x^2}{1 \text{ year}}$$

at 40° C., assuming that 0.5 years accelerate aging at 40° C. is predictive of 3 years aging at room temperature (25° C.). With such low diffusion coefficients ($10^{-18}$ m²/s at room temperature and $10^{-17}$ m²/s at 40° C. for a fiber with 40 μm diameter) the melt additive is in practical terms immobile in the polymer matrix and does not diffuse to the surface. After 3 years at room temperature or 0.5 years at 40° C. the blooming to the surface outside the defined zones is so limited (if it happens at all) that the melt additive bloom areas provided by the application of thermal energy are maintained with little to no migration.

It is believed that these low effective diffusion coefficients ("locking the melt additive in the polymer matrix") can be achieved by using melt additives in a polymer matrix with (i) no non-glassy amorphous domains or (ii) large size melt additives in a polymer matrix with a very limited portion of non-glassy amorphous domains at temperatures up to 40° C. For case (i), the polymer matrix may for example, by a completely amorphous polymer which is in its glassy state at an environmental temperature of 40° C. (i.e. Tg>40° C.). For case (ii), the polymer matrix may for example, be a semi-crystalline polymer in which a large parts or all of the amorphous domains are in the glassy state at 40° C.

One example of a suitable polymer for use in the material webs of the present invention is polypropylene. Polypropylene (PP) can have two types of amorphous domains: type I and type II. Type I can be influenced by adjacent crystalline domains and has a Tg of ~75°. ("Influenced" means that one end of the chain is still tied to the crystal.) The diffusion coefficient for melt additives in these domains is close to zero below 75° C. Type II is uninfluenced by the crystalline domains and has a Tg of ~5° C. At room temperature the melt additive is only able to effectively migrate in these uninfluenced amorphous domains (Tg ~5° C.). (When referring to the "Tg of polypropylene", the Tg of 5° C. of these uninfluenced amorphous domains is normally meant, which are not in the glassy state at room temperature.) Dependent on the portion and size of the available Type II amorphous domains, the melt additive may not be able anymore to effectively migrate in the polymer matrix, particularly if the melt additive molecules are large and bulky. In undrawn fibers, the crystals are of the form of spherolites with sufficient uninfluenced amorphous domains around. In drawn fibers (rapid cooling with rate of 2000 K/s plus stretching), fibrillous crystals form with less and smaller amorphous domains around. Large melt additives, e.g. molecular weight of GTS=891.5 g/mol, entrapped in such structure are kinetically hindered from diffusion.

With the processes described herein, it is believed that the application of heat during processing can increase the diffusion coefficient into the range of:

$$D_{\mathit{eff}} > \frac{x^2}{48 \text{ h}}$$

Achieving the above diffusion coefficient, the melt additive is able to bloom to the surface of the material web in the areas of thermal energy application with an optional post-processing curing period of up to 24 hours. If the effective diffusion coefficient of the melt additive in the polymer matrix is, for example, changed to $10^{-13}$ m²/s due to the application of thermal energy, the melt additive bloom areas may occur within 30 min for a fiber with 40 μm diameter. It is believed that the increase of the diffusion coefficient with the application of thermal energy is caused by a local change of the micro-structure of the host polymer upon application. For smaller diameter fibers and/or filaments, the melt additive bloom areas may occur even quicker than 30 minutes. Lower denier fibers may be utilized, in some forms, to promote the blooming of melt additive. For example, fiber denier may range from between 0.8 denier to 9 denier which can allow quicker blooming due to these smaller fiber cross sections.

Filament/fiber chemistry can play an important role in the migration of the melt additive through the thermoplastic polymeric material of the filament/fiber. For example, a core-sheath configuration fibers and/or filaments can be designed to promote rapid blooming. For example, the core-sheath fibers and/or filaments may comprise a first constituent polymer matrix and a second constituent polymer matrix. The first constituent polymer matrix may comprise the sheath while the second constituent polymer matrix comprise the core. These core-sheath fibers and/or filaments may be configured such that the first constituent polymer matrix is less than 50 percent by weight of the overall fibers and/or filaments while the second constituent polymer matrix is greater than 50 percent by weight. For example, a ratio by weight of the first constituent polymer matrix to the second constituent polymer matrix may be 20 percent to 80 percent; 30 percent to 70 percent, 40 percent to 60 percent or 50 percent to 50 percent, specifically including any values within these ranges and any ranges created thereby. Without wishing to be bound by theory, these configurations may promote blooming due the decreased amount of the weight percentage of the first constituent polymer matrix which means generally a thinner sheath which then correlates to a shorter diffusion distance. Where the diffusion distance of the melt additive through the sheath is not of great concern, ratios of the first constituent polymer matrix to the second constituent polymer matrix may be 50 percent to 50 percent; 60 percent to 40 percent, 70 percent to 30 percent, or 80 percent to 20 percent, specifically including all values within these ranges and any ranges created thereby.

However, in a core-sheath configuration fibers and/or filaments, melt additive provided in the sheath may diffuse into the core over time even if the material web is stored in ambient conditions. It is believed that this is due to the concentration gradient of melt additive between the sheath and the core. And, as a consequence, the concentration of the melt additive on the surface of the fiber also decreases over time and the desired property of the surface (hydrophilicity or softness) gets weaker over time.

To combat this problem, in some forms, the same melt additive may be applied to both the core and the sheath in the same concentration to avoid the concentration gradient. In other forms of the present invention, the high glass transition temperature of polyethylene terephthalate (ranging from 67 to 81° C., dependent on the grade) can be leveraged to create a kinetic barrier against diffusion as long as the environmental temperature is below the glass transition temperature of polyethylene terephthalate. So the polyethylene terephthalate core does not need to contain melt additive, which reduces the cost. Alternative suitable polymers with Tg above ambient temperature are copolyethylene terephthalate or Polylactic acid.

Generally, selection of the core component of sheath-core filaments and/or fibers may comprise a higher melting temperature than the sheath component. For example, the core component may have a melting temperature which is greater than 30 degrees C. of the melting temperature of the sheath component. In some forms, the core component may comprise a melting temperature which is greater than about 40 degrees C. of the melting temperature of the sheath component. The difference in melting temperature between the core and the sheath, in some forms, can be at least 20° C., or 30 to 50° C., specifically including all values within these ranges and any ranges created thereby.

Selection of the material via melting point as described herein can discourage the diffusion of the melt additive into the core even via thermal processing. For example, during air through bonding, such selection of melting temperatures can ensure that the sheath component melts to some extent while the core material does not. However, if the selection of the melting temperature is too high, then the melt additive in the sheath could be thermally degraded. For example, during formation of the filaments and/or fibers, both components would need to be at a temperature which is about the melting temperature of the core component to allow processing of the core component and the sheath component. As such, if the melting temperature of the core component is selected to be too high, then the melt additive may suffer from thermal degradation. So, careful selection of the components and the melt additive should be exercised as described herein. By using a co-poly ethylene terephthalate with a low melting point (~160°) instead of poly ethylene terephthalate (melting point ~250° C.), the present invention enables to use polyethylene (melting point ~120° C.) in combination with a variety of otherwise thermally unstable melt additives.

Such migration from one polymer matrix to a second polymer matrix in bi-component fibers and/or filaments may be problematic for side-by-side configurations in addition to core-sheath configurations. In side-by-side configurations, the melt temperatures of the constituent materials may be selected as described herein to discourage migration of the melt additive from one constituent material polymer matrix to the other. Similarly, the melt additives may be selected as described herein to either auto bloom or to selectively bloom based upon energy application either across the entirety of the web or in a plurality of discrete locations.

Indeed, such migration of melt additive from the surface of the fibers and/or filaments can be a significant issue. For example, where the material webs of the present invention comprise a hydrophilic melt additive and such material webs are utilized as acquisition, distribution, or secondary topsheet layers, the migration of hydrophilic bloom areas on the surface of the fibers and/or filaments could cause a failure of the article. As such, it is of great benefit for the material webs, in this particular form, to stay hydrophilic over time.

If standard surfactant coatings are applied to such web (e.g. via a kiss roll application) the hydrophilicity can drop significantly over time (within around 6 months), due to migration of the surfactant coating into the fibers and/or filaments. However, it is believed that a blooming melt additive can overcome this limitation if the blooming melt additive is incompatible with the polymer matrix at the temperature at which the blooming is supposed to happen and at all temperature below. If the blooming happens at ambient temperature or above, there is a thermodynamic driving force that makes the melt additive leave the polymer towards the surface. And, even if the melt additive should be removed from the surface, it will be replenished from the reservoir inside the fiber.

With regard to some specific examples, the inventors have found that without the application of thermal energy to certain combinations of materials, there is little blooming that occurs. Example 1: polypropylene and polyvel 351 (from Polyvel Inc.); Example 2: polypropylene and Unithox 720 or Unithox 750 (from Baker Hughes); Example 3:

polylactic acid and Unithox 720 or Unithox 750 (from Baker Hughes). Example 4: Polypropylene with Span 20 or Span 40 (both from Merck). It is believed that these melt additives in combination with polyethylene would yield similar results absent the application of thermal energy.

Precursor Material

The material webs of the present invention begin with the constituent material. As noted previously, the material webs of the present invention may comprise any suitable material for example, nonwoven webs or laminates created therefrom. Where the material webs of the present invention comprise laminates, the laminates may comprise a plurality of nonwoven layers. Additional forms are contemplated where the material webs of the present invention comprise a nonwoven web comprising multiple nonwoven strata. Regardless of the form of the material web, any suitable material may be utilized.

For those forms where the material webs comprise a nonwoven, any suitable thermoplastic polymer may be utilized. Some suitable thermoplastic polymers are polymers that melt and then, upon cooling, crystallize or harden, but can be re-melted upon further heating. Suitable thermoplastic polymers used herein have a melting temperature (also referred to as solidification temperature) from about 60° C. to about 300° C., from about 80° C. to about 250° C., or from 100° C. to 215° C.

The thermoplastic polymers can be derived any suitable material including renewable resources (including bio-based and recycled materials), fossil minerals and oils, and/or biodegradable materials. Some suitable examples of thermoplastic polymers include polyolefins, polyesters, polyamides, copolymers thereof, and combinations thereof. Some exemplary polyolefins include polyethylene or copolymers thereof, including low density, high density, linear low density, or ultra low density polyethylenes such that the polyethylene density ranges between 0.90 grams per cubic centimeter to 0.97 grams per cubic centimeter, between 0.92 and 0.95 grams per cubic centimeter or any values within these ranges or any ranges within these values. The density of the polyethylene may be determined by the amount and type of branching and depends on the polymerization technology and co-monomer type.

Some suitable examples of polypropylene and/or polypropylene copolymers, include atactic polypropylene; isotactic polypropylene, syndiotactic polypropylene, and combination thereof, "hereafter propylene polymers" can also be used. Polypropylene copolymers, especially ethylene can be used to lower the melting temperature and improve properties. These polypropylene polymers can be produced using metallocene and Ziegler-Natta catalyst systems. These polypropylene and polyethylene compositions can be combined together to optimize end-use properties. Polybutylene is also a useful polyolefin and may be used in some embodiments. Other suitable polymers include polyamides or copolymers thereof, such as Nylon 6, Nylon 11, Nylon 12, Nylon 46, Nylon 66; polyesters or copolymers thereof, such as maleic anhydride polypropylene copolymer, polyethylene terephthalate; olefin carboxylic acid copolymers such as ethylene/acrylic acid copolymer, ethylene/maleic acid copolymer, ethylene/methacrylic acid copolymer, ethylene/vinyl acetate copolymers or combinations thereof; poly-lactic acid; polyacrylates, polymethacrylates, and their copolymers such as poly(methyl methacrylates).

Non-limiting examples of suitable commercially available polypropylene or polypropylene copolymers include Basell Profax PH-835 (a 35 melt flow rate Ziegler-Natta isotactic polypropylene from Lyondell-Basell), Basell Metocene MF-650W (a 500 melt flow rate metallocene isotactic polypropylene from Lyondell-Basell), Moplen, HP2833, HP462R and S, HP551R, HP552N, HP552R, HP553R, HP561R, HP563S, HP567P, HP568S, RP3231, Polybond 3200 (a 250 melt flow rate maleic anhydride polypropylene copolymer from Crompton), Exxon Achieve 3854 (a 25 melt flow rate metallocene isotactic polypropylene from Exxon-Mobil Chemical), Mosten NB425 (a 25 melt flow rate Ziegler-Natta isotactic polypropylene from Unipetrol), Danimer 27510 (a polyhydroxyalkanoate polypropylene from Danimer Scientific LLC), Achieve 3155 (a 35 melt flow rate Ziegler-Natta isotactic polypropylene from Exxon Mobil).

In some forms, the thermoplastic polymer can be selected from the group consisting of polypropylene, polyethylene, polypropylene co-polymer, polyethylene co-polymer, polyethylene terephthalate, polybutylene terephthalate, polylactic acid, polyhydroxyalkanoates, polyamide-6, polyamide-6,6, and combinations thereof. The polymer can be polypropylene based, polyethylene based, polyhydroxyalkanoate based polymer systems, copolymers and combinations thereof.

Biodegradable thermoplastic polymers also are contemplated for use herein. Biodegradable materials are susceptible to being assimilated by microorganisms, such as molds, fungi, and bacteria when the biodegradable material is buried in the ground or otherwise contacts the microorganisms (including contact under environmental conditions conducive to the growth of the microorganisms). Suitable biodegradable polymers also include those biodegradable materials which are environmentally-degradable using aerobic or anaerobic digestion procedures, or by virtue of being exposed to environmental elements such as sunlight, rain, moisture, wind, temperature, and the like. The biodegradable thermoplastic polymers can be used individually or as a combination of biodegradable or non-biodegradable polymers. Biodegradable polymers include polyesters containing aliphatic components. Among the polyesters are ester polycondensates containing aliphatic constituents and poly(hydroxycarboxylic) acid. The ester polycondensates include diacids/diol aliphatic polyesters such as polybutylene succinate, polybutylene succiate co-adipate, aliphatic/aromatic polyesters such as terpolymers made of butylenes diol, adipic acid and terephthalic acid. The poly(hydroxycarboxylic) acids include lactic acid based homopolymers and copolymers, polyhydroxybutyrate (PHB), or other polyhydroxyalkanoate homopolymers and copolymers. Such polyhydroxyalkanoates include copolymers of PHB with higher chain length monomers, such as $C_6$-$C_{12}$, and higher, polyhydroxyalkanaotes, such as those disclosed in U.S. Pat. Nos. RE 36,548 and 5,990,271.

An example of a suitable commercially available polylactic acid is NATUREWORKS from Cargill Dow™ sold under the trade names 6202D, 6100D, 6252D and 6752D and 6302D and LACEA from Mitsui Chemical. An example of a suitable commercially available diacid/diol aliphatic polyester is the polybutylene succinate/adipate copolymers sold as BIONOLLE 1000 and BIONOLLE 3000 from the Showa High Polymer Company, Ltd. (Tokyo, Japan). An example of a suitable commercially available aliphatic/aromatic copolyester is the poly(tetramethylene adipate-co-terephthalate) sold as EASTAR BIO Copolyester from Eastman Chemical or ECOFLEX from BASF.

The thermoplastic polymer component can be a single polymer species as described above or a blend of two or more thermoplastic polymers as described above, e.g. two different polypropylene resins. As an example, the constituent fibers and/or filaments of the first nonwoven layer can be comprised of polymers such as polypropylene and blends of polypropylene and polyethylene. The second nonwoven layer may comprise fibers and/or filaments selected from polypropylene, polypropylene/polyethylene blends, and polyethylene/polyethylene teraphthalate blends. In some forms, the second nonwoven layer may comprise fibers selected from cellulose rayon, cotton, other hydrophilic fiber materials, or combinations thereof. The fibers can also comprise a super absorbent material such as polyacrylate or any combination of suitable materials.

The fibers and/or filaments of the first nonwoven layer and/or the second nonwoven layer can be monocomponent, bi-component, and/or bi-constituent, round or non-round (e.g., capillary channel fibers), and can have major cross-sectional dimensions (e.g., diameter for round fibers) ranging from 0.1-500 microns. The constituent fibers and/or filaments of the nonwoven precursor web may also be a mixture of different fiber types, differing in such features as chemistry (e.g. polyethylene and polypropylene), components (mono- and bi-), denier (micro denier and >2 denier), shape (i.e. capillary and round) and the like. The constituent fibers and/or filaments can range from about 0.1 denier to about 100 denier.

As used herein, the term "monocomponent" fiber refers to a fiber formed from one extruder using one or more polymers. This is not meant to exclude fibers and/or filaments formed from one polymer to which small amounts of additives have been added for coloration, antistatic properties, lubrication, hydrophilicity, etc.

As used herein, the term "bi-component fibers" or "bi-component filaments" refer to fibers and/or filaments which have been formed from at least two different polymers extruded from separate extruders but spun together to form one fiber. Bi-component fibers are also sometimes referred to as conjugate fibers or multicomponent fibers. The polymers are arranged in substantially constantly positioned distinct zones across the cross-section of the bi-component fibers and extend continuously along the length of the bi-component fibers. The configuration of such a bi-component fiber may be, for example, a sheath/core arrangement wherein one polymer is surrounded by another, or may be a side-by-side arrangement, a pie arrangement, or an "islands-in-the-sea" arrangement. Some specific examples of fibers which can be used in the first nonwoven layer include polyethylene/polypropylene side-by-side bi-component fibers. Another example, is a polypropylene/polyethylene bi-component fiber where the polyethylene is configured as a sheath and the polypropylene is configured as a core within the sheath. Still another example, is a polypropylene/polypropylene bi-component fiber where two different propylene polymers are configured in a side-by-side configuration.

Bi-component fibers may comprise two different resins, e.g. a first polypropylene resin and a second polypropylene resin. The resins may have different melt flow rates, molecular weights, or molecular weight distributions. Ratios of the 2 different polymers may be about 50/50, 60/40, 70/30 or any ratio within these ratios. The ratio may be selected to control the amount of crimp, strength of the nonwoven layer, softness, bonding or the like.

As used herein, the term "bi-constituent fibers" or "bi-constituent filaments" refer to fibers and/or filaments which have been formed from at least two polymers extruded from the same extruder as a blend. Bi-constituent fibers do not have the various polymer components arranged in relatively constantly positioned distinct zones across the cross-sectional area of the fiber and the various polymers are usually not continuous along the entire length of the fiber, instead usually forming fibrils which start and end at random. Bi-constituent fibers are sometimes also referred to as multi-constituent fibers. In other examples, a bi-component fiber may comprise a multi-constituent components.

As used herein, the term "non-round fibers" or "non-round filaments" describe fibers and/or filaments having a non-round cross-section, and includes "shaped fibers" and "capillary channel fibers." Such fibers can be solid or hollow, and they can be tri-lobal, delta-shaped, and can be fibers having capillary channels on their outer surfaces. The capillary channels can be of various cross-sectional shapes such as "U-shaped", "H-shaped", "C-shaped" and "V-shaped". One practical capillary channel fiber is T-401, designated as 4DG fiber available from Fiber Innovation Technologies, Johnson City, Tenn. T-401 fiber is a polyethylene terephthalate (PET polyester).

Further regarding coloration, the first layer and/or the second layer may comprise pigments, inks or dyes to achieve any color difference as provided herein. The fibers and/or filaments of the first layer and the fibers and/or filaments of the second layer may differ from each other in pigmentation. As used herein, to "differ in pigmentation" "difference in pigmentation" means (a) the fibers and/or filaments of the first layer comprise a pigment which is different from the pigment of the second layer; or (b) the fibers and/or filaments of the first layer comprise a different combination of pigments; or (c) the fibers and/or filaments of the first layer comprise different amounts of the same pigment(s) versus the second layer; or (d) combinations of any of options a) to c). The pigment or colorant may be added uniformly throughout the fibers and/or filaments within each layer or may be added to one or both components in same or different type/amount within multicomponent fibers and/or filaments.

A pigment is a material, which can be organic or inorganic and may include activatable, structural and or special effects pigments. A pigment changes the color of reflected or transmitted light as the result of wavelength-selective absorption. This physical process differs from fluorescence, phosphorescence, and other forms of luminescence, in which a material emits light. A pigment is a generally insoluble powder, which differs from a dye, which either is itself a liquid or is soluble in a solvent (resulting in a solution). Dyes are often used to provide a print on the surface of a nonwoven web, such as graphics, pattern or images. Hence, these dyes do not form a part of the fibers and/or filaments of the nonwoven web but are rather applied on the web surface. In the present invention the pigments may be comprised within the fibers and/or filaments of the multilayered nonwoven web, which eliminates the risk of rub-off or wash-off of the color(s) imparted to the multilayered nonwoven web by the pigment.

For the present invention, the pigment will typically be mixed with the thermoplastic material, of which the fibers and/or filaments are made. Often, the pigment is added to the thermoplastic material in the form of a master batch or concentrate at the time of formation of the fibers and/or filaments. Colored master batches useful for the present invention include polypropylene based custom color master batches e.g. supplied by Ampacet; Lufilen and Luprofil supplied by BASF; Remafin for polyolefin fibers and/or filaments, Renol-AT for polyester fibers and/or filaments, Renol-AN for polyamide fibers and/or filaments and CESA for renewable polymers supplied by Clariant. Hence, the pigment will be suspended in the molten thermoplastic material prior to the thermoplastic material being forced through the spinnerets to form and lay down the fibers and/or filaments which form the nonwoven web.

To increase the whiteness and/or opacity of the fibers and/or filaments in either or both layers, titanium dioxide (TiO2) may be used. Different crystal forms are available, however most preferred are rutile or anatase TiO2. Other white pigments include zinc oxide, zinc sulfide, lead carbonate or calcium carbonate. To create a black color, carbon black or any other suitable colorant may be used. Various colored inorganic pigments may be used depending upon the desired color and may include metal oxides, hydroxides and sulfides or any other suitable material. Non-limiting examples of inorganic pigments include cadmium orange, iron oxide, ultramarine, chrome oxide green. One or more pigments may be combined to create the desired color. Non-limiting examples of organic colorants include anthraquinone pigments, azo pigments, benzimidazolone pigments, BONA Lakes, Dioxazine, Naphthol, Perylene, Perinone, Phthalocyanine, Pyranthrone, Quinacridones. Effects pigments including metal, pearlescent and fluorescent may also be used. Various colorants are described in *Plastics Additives Handbook,* 5th Edition.

The nonwoven materials suitable for use in the material webs of the present invention may be made from any suitable process. For example, as noted previously, the material web may comprise nonwoven layers or nonwoven strata produced via a spunbond process, or carded webs comprising staple fibers.

Forms of the present invention are contemplated where fillers—having a higher thermal conductivity than the polymer material—are included to the polymer material. Exemplary fillers include inorganic fillers such as calcium carbonate, which can have a higher thermal conductivity than the polymer matrix (e.g., than polypropylene), allowing faster and more homogeneous transfer of heat within the fiber matrix. This can allow for more benefit from the heat already applied in the processing of the material web and, if any, may increase the effect of heat treatment after the production of the material web. The particle size of the filler may be important for the observed effect. In one embodiment, the average particle size of the filler is hence 10 μm or smaller, or 1 μm or smaller (ISO 14688). The material may also be chosen to exhibit a thermal conductivity at room temperature of 1 W·m-1·K-1 or greater or more, 2.0 W·m-1·K-1 or more (DIN EN 12664). In some forms, the thermal conductivity could be 2.7 W·m-1·K-1, which approximately corresponds to that of CaCO3. Suitable CaCO3 can in one example be either ground CaCO3 (GCC) or precipitated CaCO3, or a combination thereof. For example, the CaCO3 can be micro-CaCO3 (GCC) having a Plus 325 Mesh of 0.002% and/or mean particle size of 1.6 microns and/or specific surface area of 4.5 m2/g. Such material is, for example, contained in a masterbatch under the trade name "Fiberlink 201S" from A. Schulman. In another example, the CaCO3 can be nano-CaCO3 (PCC) having a residue on sieve 45 micron <250 ppm and/or mean particle diameter of 0.07-0.13 microns and/or specific surface area 16 m2/g. Such material is, for example, found under the tradename SOCAL® U1S2 from Imerys Group. The use of CaCO3 at around 10 percent by weight boosted blooming in materials tested. However, because of its size, CaCO3 may not be appropriate for other types of material processing, e.g. meltblowing.

Disposable Absorbent Articles

The material webs of the present invention may comprise any suitable portion of a disposable absorbent article, e.g. secondary topsheet, acquisition layer, distribution layer.

Figure 2:
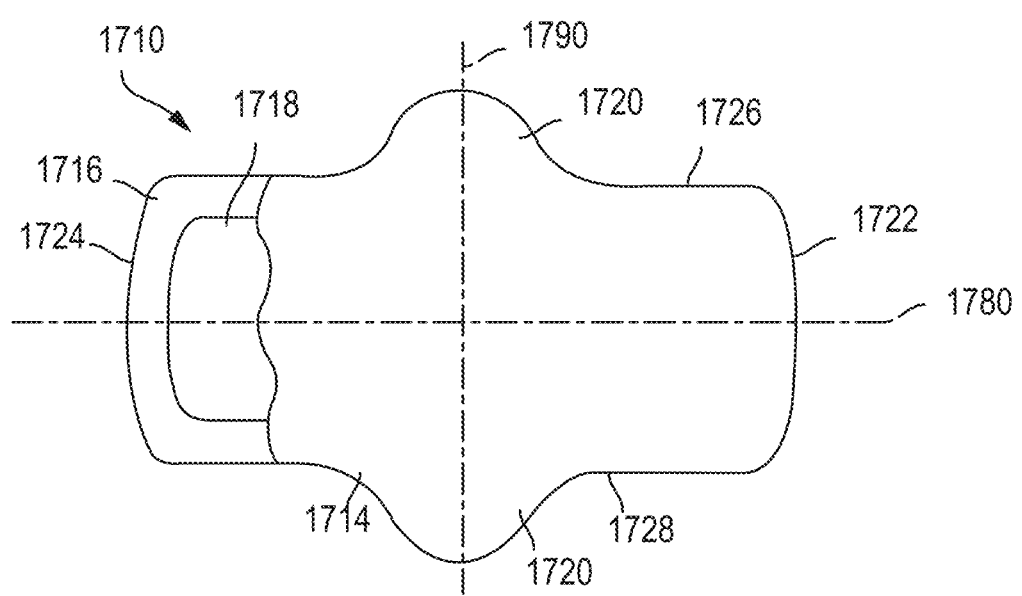
FIG. 2 is a top view of a feminine hygiene article, i.e. sanitary napkin, constructed in accordance with the present disclosure.

Referring to FIG. 2, an absorbent article 1710 which may utilize the material webs described herein may be a sanitary napkin/feminine hygiene pad. As shown, the sanitary napkin 1710 may comprise a liquid permeable topsheet 1714, a liquid impermeable, or substantially liquid impermeable, backsheet 1716, and an absorbent core 1718 positioned intermediate the topsheet 1714 and the backsheet 1716. The sanitary napkin 1710 may comprise wings 1720 extending outwardly with respect to a longitudinal axis 1780 of the sanitary napkin 1710. The sanitary napkin 1710 may also comprise a lateral axis 1790. The wings 1720 may be joined to the topsheet 1714, the backsheet 1716, and/or the absorbent core 1718. The sanitary napkin 1710 may also comprise a front edge 1722, a rear edge 1724 longitudinally opposing the front edge 1722, a first side edge 1726, and a second side edge 1728 laterally opposing the first side edge 1726. The longitudinal axis 1780 may extend from a midpoint of the front edge 1722 to a midpoint of the rear edge 1724. The lateral axis 1790 may extend from a midpoint of the first side edge 1726 to a midpoint of the second side edge 1728. The sanitary napkin 1710 may also be provided with additional features commonly found in sanitary napkins as is known in the art. In some forms of the present invention, the wings may be provided with zones of extensibility as described in U.S. Pat. No. 5,972,806.

Any suitable absorbent core known in the art may be utilized. The absorbent core 1718 may be any absorbent member which is generally compressible, conformable, non-irritating to the wearer's skin, and capable of absorbing and retaining liquids such as urine, menses, and/or other body exudates. The absorbent core 1718 may be manufactured from a wide variety of liquid-absorbent materials commonly used in disposable absorbent articles such as comminuted wood pulp which is generally referred to as airfelt. The absorbent core 1718 may comprise superabsorbent polymers (SAP) and less than 15%, less than 10%, less than 5%, less than 3%, or less than 1% of airfelt, or be completely free of airfelt. Examples of other suitable absorbent materials comprise creped cellulose wadding, meltblown polymers including conform, chemically stiffened, modified or cross-linked cellulosic fibers, tissue including tissue wraps and tissue laminates, absorbent foams, absorbent sponges, superabsorbent polymers, absorbent gelling materials, or any equivalent material or combinations of materials.

The configuration and construction of the absorbent core 1718 may vary (e.g., the absorbent core may have varying caliper zones, a hydrophilic gradient, a superabsorbent gradient, or lower average density and lower average basis weight acquisition zones; or may comprise one or more layers or structures). In some forms, the absorbent core 1718 may comprise one or more channels, such as two, three, four, five, or six channels.

The absorbent core 1718 of the present disclosure may comprise one or more adhesives, for example, to help immobilize the SAP or other absorbent materials within a core wrap and/or to ensure integrity of the core wrap, in particular when the core wrap is made of two or more substrates. The core wrap may extend to a larger area than required for containing the absorbent material(s) within.

Absorbent cores comprising relatively high amounts of SAP with various core designs are disclosed in U.S. Pat. No. 5,599,335 to Goldman et al., EP 1,447,066 to Busam et al., WO 95/11652 to Tanzer et al., U.S. Pat. Publ. No. 2008/0312622A1 to Hundorf et al., and WO 2012/052172 to Van Malderen.

Other forms and more details regarding channels and pockets that are free of, or substantially free of absorbent materials, such as SAP, within absorbent cores are discussed in greater detail in U.S. Patent Application Publication Nos. 2014/0163500, 2014/0163506, and 2014/0163511, all published on Jun. 12, 2014.

The absorbent article 1710 may comprise additional layers between the top sheet 1714 and the absorbent core 1718. For example, the absorbent article 1710 may comprise a secondary topsheet and/or an acquisition layer positioned between the topsheet 1714 and the absorbent core 1718.

The backsheet can comprise a liquid impervious film. The backsheet can be impervious to liquids (e.g., body fluids) and can be typically manufactured from a thin plastic film. However, typically the backsheet can permit vapours to escape from the disposable article. In an embodiment, a microporous polyethylene film can be used for the backsheet. A suitable microporous polyethylene film is manufactured by Mitsui Toatsu Chemicals, Inc., Nagoya, Japan and marketed in the trade as PG-P.

One suitable material for the backsheet can be a liquid impervious thermoplastic film having a thickness of from about 0.012 mm (0.50 mil) to about 0.051 mm (2.0 mils), for example including polyethylene or polypropylene. Typically, the backsheet can have a basis weight of from about 5 g/m$^2$ to about 35 g/m$^2$. However, it should be noted that other flexible liquid impervious materials may be used as the backsheet. Herein, "flexible" refers to materials which are compliant and which will readily conform to the general shape and contours of the wearer's body.

The backsheet can be typically positioned adjacent an outer-facing surface of the absorbent core and can be joined thereto by any suitable attachment device known in the art. For example, the backsheet may be secured to the absorbent core by a uniform continuous layer of adhesive, a patterned layer of adhesive, or an array of separate lines, spirals, or spots of adhesive. Illustrative, but non-limiting adhesives, include adhesives manufactured by H. B. Fuller Company of St. Paul, Minn., U.S.A., and marketed as HL-1358J. An example of a suitable attachment device including an open pattern network of filaments of adhesive is disclosed in U.S. Pat. No. 4,573,986 entitled "Disposable Waste-Containment Garment", which issued to Minetola et al. on Mar. 4, 1986. Another suitable attachment device including several lines of adhesive filaments swirled into a spiral pattern is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Alternatively, the attachment device may include heat bonds, thermal fusion bonds, pressure bonds, ultrasonic bonds, dynamic mechanical bonds, or any other suitable attachment device or combinations of these attachment devices. The backsheet may be additionally secured to the topsheet by any of the above-cited attachment devices/methods.

Still another example of a disposable absorbent article which may utilize the material webs of the present invention are diapers which include non-refastenable pants, re-fastenable pants and/or re-fastenable diapers. Diapers have can have a similar construction to that of sanitary napkins. An exemplary diaper is described below.

Figure 3:
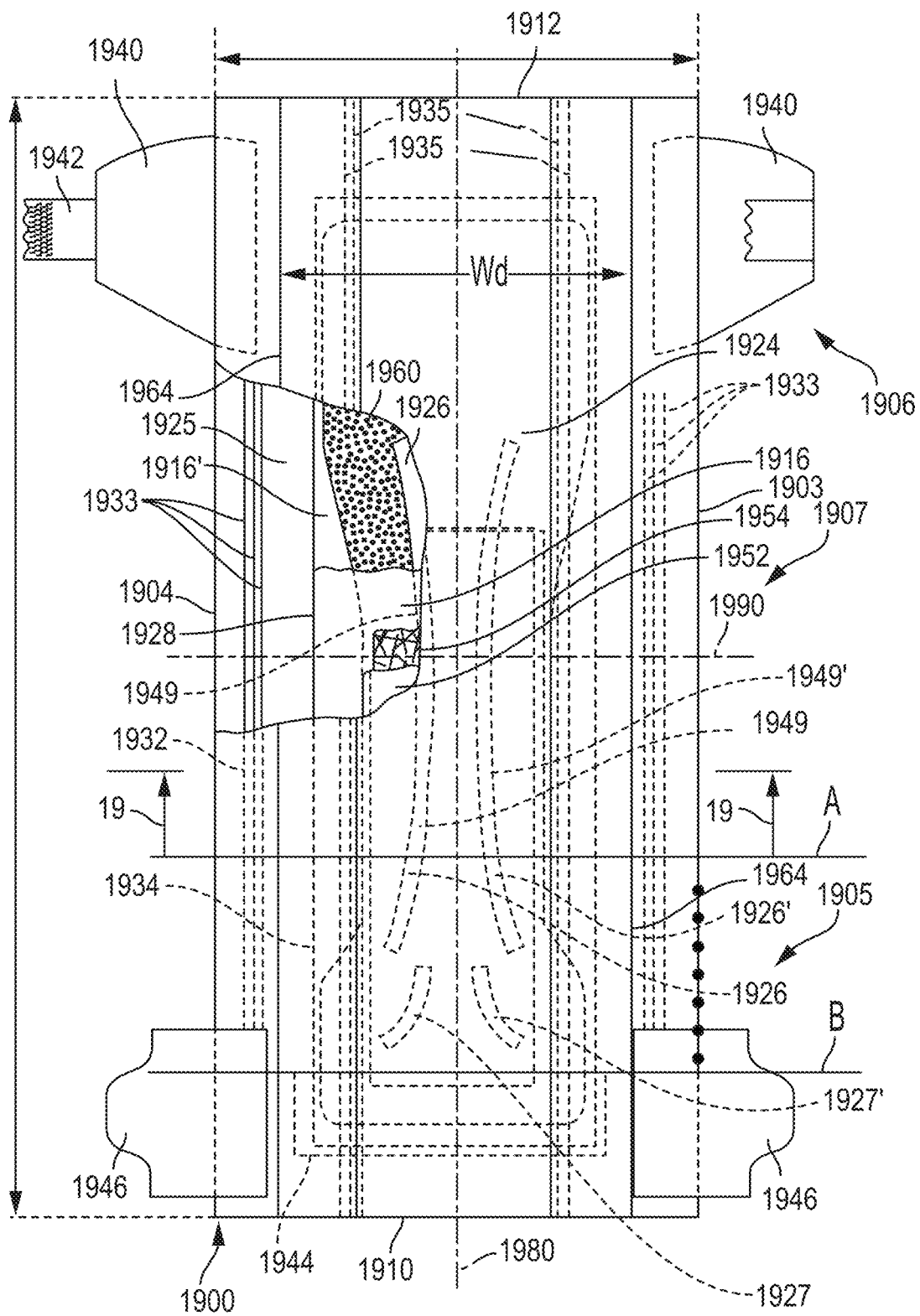
FIG. 3 is a top view of an absorbent article with some layers partially removed in accordance with the present disclosure.

Referring to FIG. 3, a plan view of an example absorbent article that is a diaper 1900 in its flat-out, uncontracted state (i.e., with elastic induced contraction pulled out) with portions of the structure being cut-away to more clearly show the construction of the diaper 1900 and with its wearer-facing surface toward the viewer. This diaper is shown for illustration purpose only as the present disclosure may be used for making a wide variety of diapers and other absorbent articles.

The absorbent article may comprise a liquid permeable topsheet 1924, a liquid impermeable backsheet 1925, an absorbent core 1928 positioned at least partially intermediate the topsheet 1924 and the backsheet 1925, and barrier leg cuffs 1934. The absorbent article may also comprise a liquid management system ("LMS") 1950 (shown in FIG. 4), which, in the example represented, comprises a distribution layer 1954 and an acquisition layer 1952 that will both be further discussed below. In various forms, the acquisition layer 1952 may instead distribute bodily exudates and the distribution layer 1954 may instead acquire bodily exudates or both layers may distribute and/or acquire bodily exudates. The LMS 1950 may also be provided as a single layer or two or more layers. The absorbent article may also comprise elasticized gasketing cuffs 1932 joined to the chassis of the absorbent article, typically via the topsheet and/or backsheet, and substantially planar with the chassis of the diaper.

The Figures also show typical taped diaper components such as a fastening system comprising adhesive tabs 1942 or other mechanical fasteners attached towards the rear edge of the absorbent article 1900 and cooperating with a landing zone on the front of the absorbent article 1900. The absorbent article may also comprise other typical elements, which are not represented, such as a rear elastic waist feature and a front elastic waist feature, for example.

The absorbent article 1900 may comprise a front waist edge 1910, a rear waist edge 1912 longitudinally opposing the front waist edge 1910, a first side edge 1903, and a second side edge 1904 laterally opposing the first side edge 1903. The front waist edge 1910 is the edge of the absorbent article 1900 which is intended to be placed towards the front of the user when worn, and the rear waist edge 1912 is the opposite edge. Together the front waist edge 1910 and the rear waist edge form waist opening when the absorbent article 1900 is donned on a wearer. The absorbent article 1900 may have a longitudinal axis 1980 extending from the lateral midpoint of the front waist edge 1910 to a lateral midpoint of the rear waist edge 1912 of the absorbent article 1900 and dividing the absorbent article 1900 in two substantially symmetrical halves relative to the longitudinal axis 1980, with article placed flat and viewed from the wearer-facing surface as illustrated FIG. 4. The absorbent article may also have a lateral axis 1990 extending from the longitudinal midpoint of the first side edge 1903 to the longitudinal midpoint of the second side edge 1904. The length L of the absorbent article 1900 may be measured along the longitudinal axis 1980 from the front waist edge 1910 to the rear waist edge 1912. The crotch width of the absorbent article 1900 may be measured along the lateral axis 1990 from the first side edge 1903 to the second side edge 1904. The absorbent article 1900 may comprise a front waist region 1905, a rear waist region 1906, and a crotch region 1907. The front waist region, the rear waist region, and the crotch region each define ⅓ of the longitudinal length of the absorbent article. Front and back portions may also be defined on opposite sides of the lateral axis 1990.

The topsheet 1924, the backsheet 1925, the absorbent core 1928, and the other article components may be assembled in a variety of configurations, in particular by gluing or heat embossing, for example. Example diaper configurations are described generally in U.S. Pat. Nos. 3,860,003, 5,221,274, 5,554,145, 5,569,234, 5,580,411, and 6,004,306.

The absorbent core 1928 may comprise an absorbent material comprising 75% to 100%, at least 80%, at least 85%, at least 90%, at least 95%, or at least 99%, all by weight, of the absorbent material, specifically reciting all 0.1% increments within the above-specified ranges and all ranges formed therein or thereby, and a core wrap enclosing the absorbent material. The core wrap may typically comprise two materials, substrates, or nonwoven materials 16 and 16' for the top side and bottom side of the core.

Figure 4:
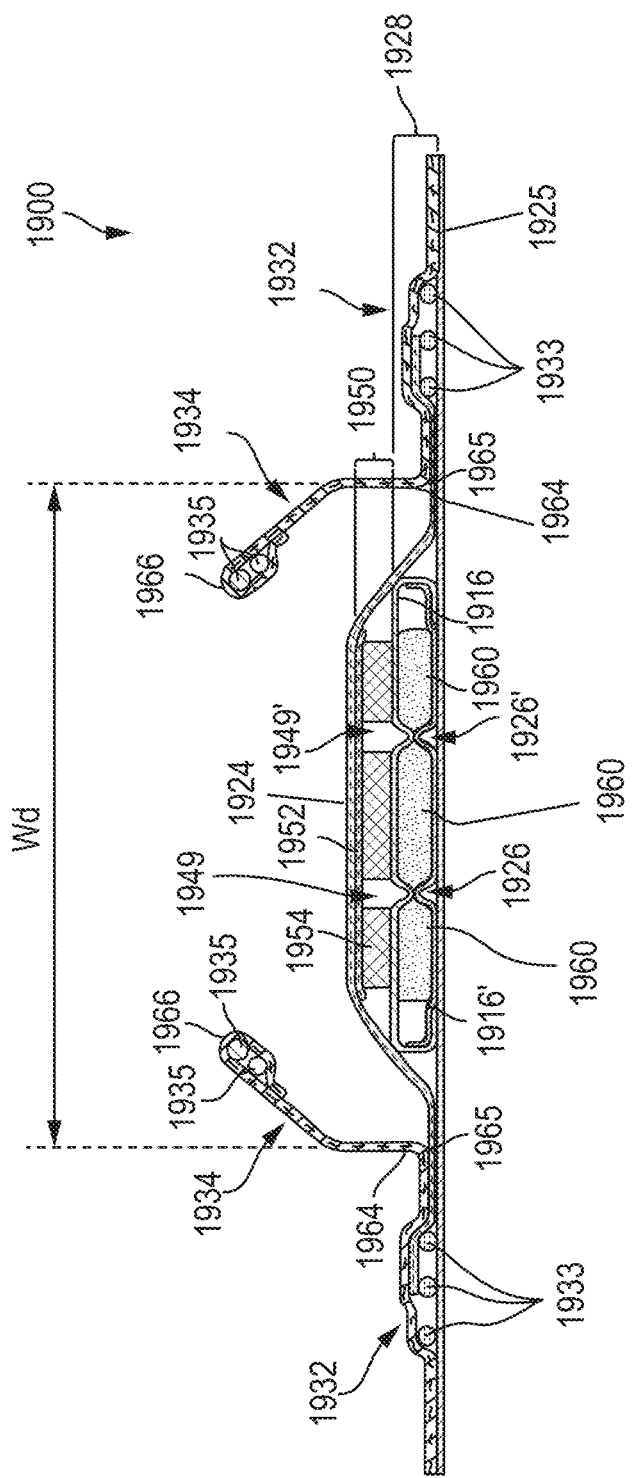
FIG. 4 is a cross-sectional view of the absorbent article taken about line 19-19 of FIG. 3 in accordance with the present disclosure.
Figure 5:
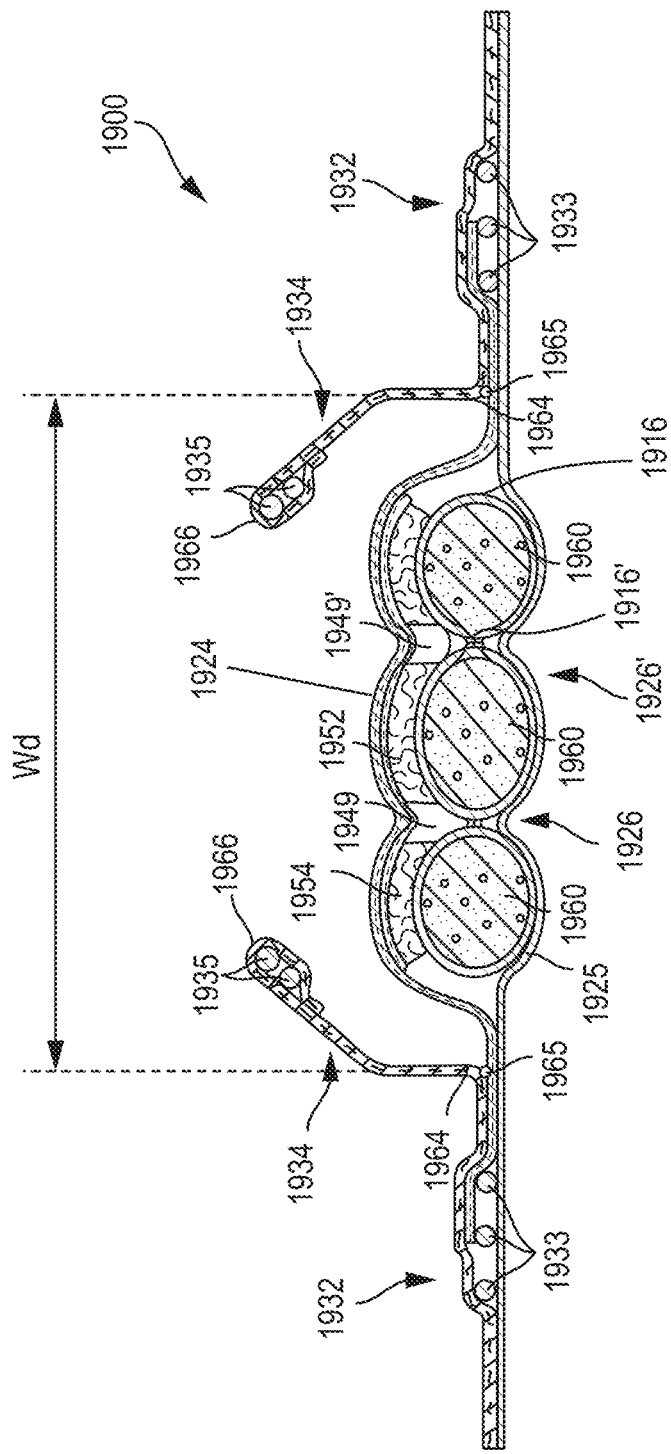
FIG. 5 is a view of the absorbent article of FIG. 4 where the absorbent article has been at least partially loaded with fluid in accordance with the present disclosure.
Figure 6A:
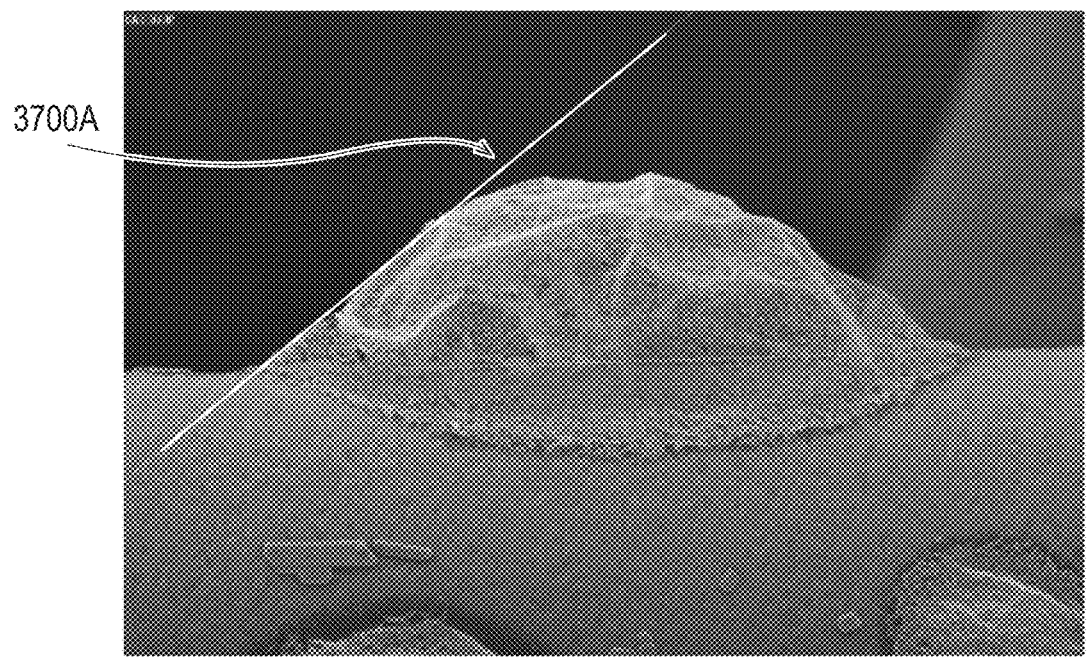
FIGS. 6A-9B are photomicrographs depicting exemplary water droplets on fibers for the SEM contact angle measurement method disclosed herein.
Figure 6B:
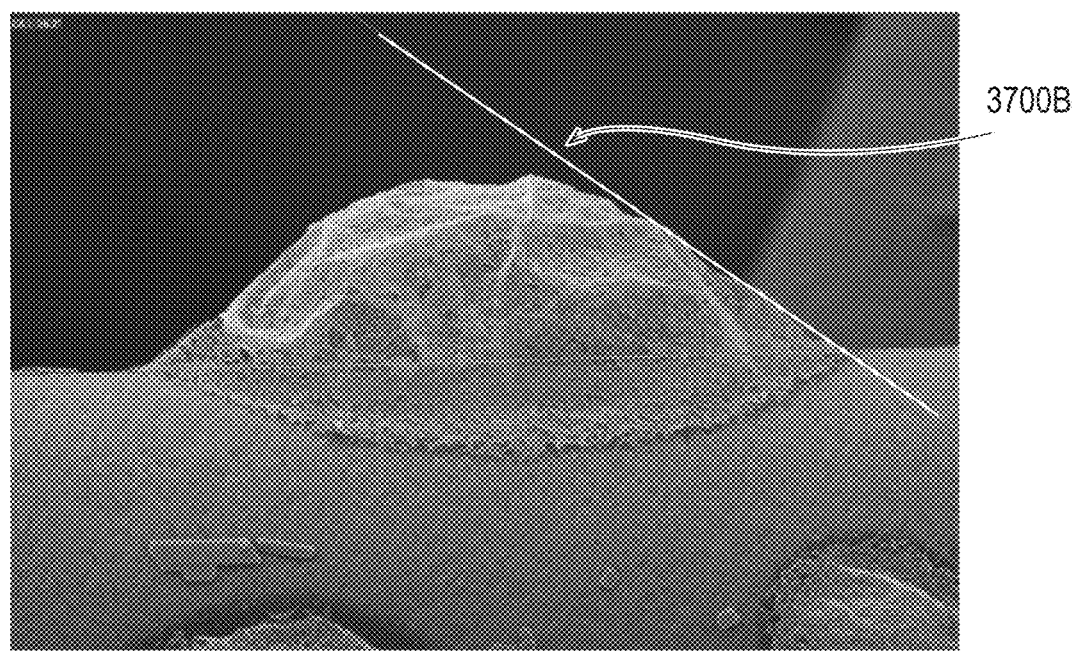
Figure 7A:
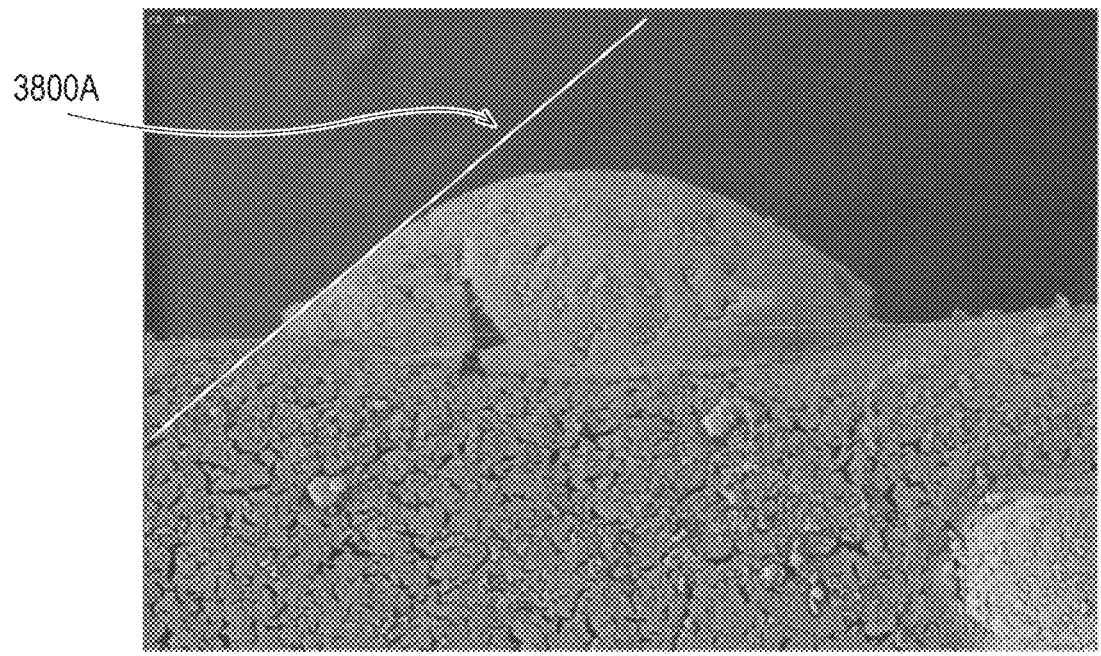
Figure 7B:
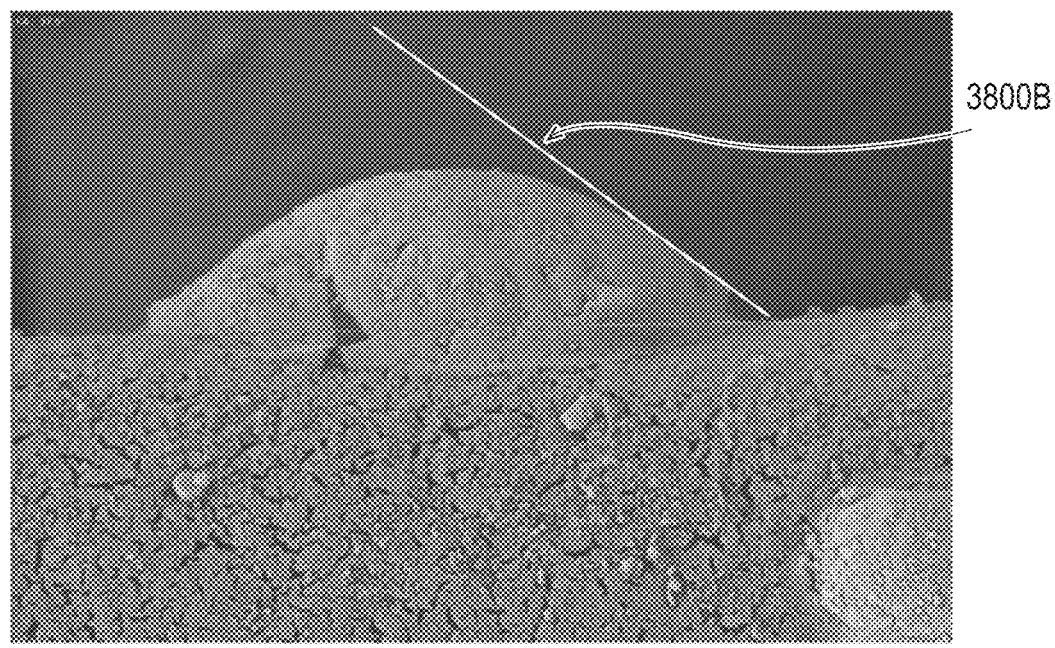
Figure 8A:
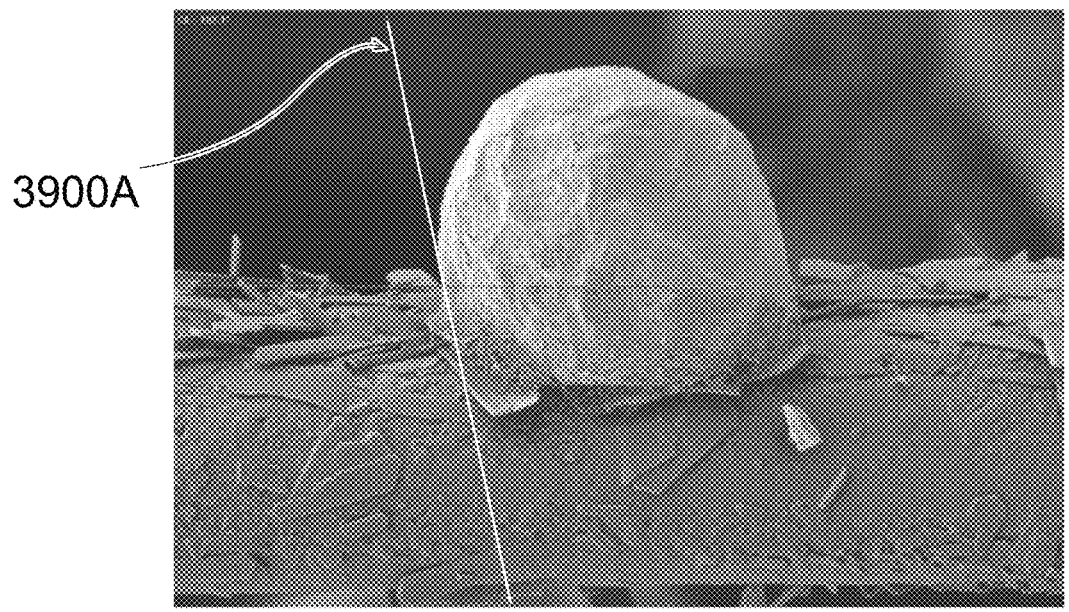
Figure 8B:
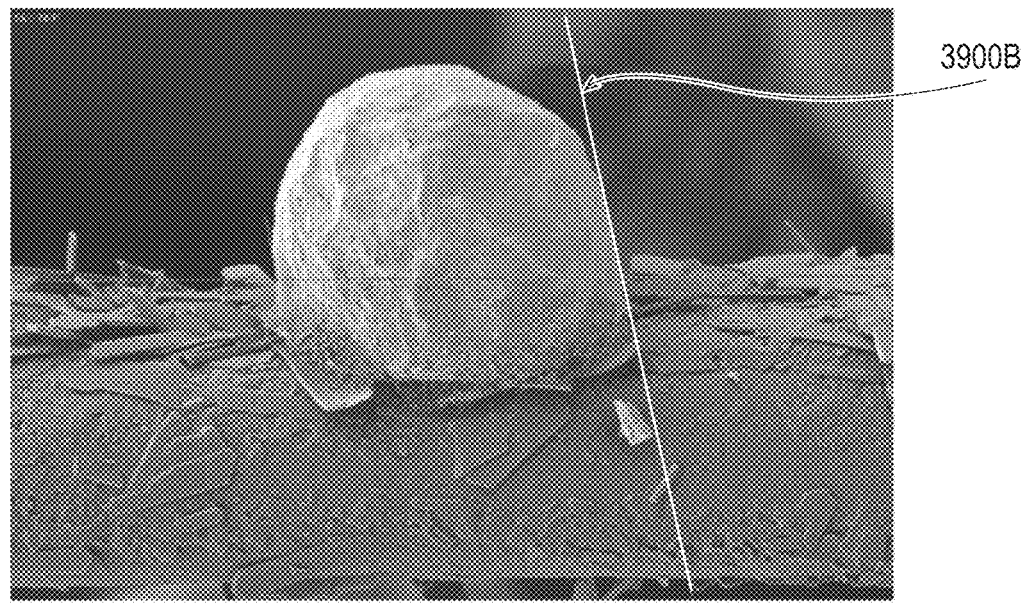

The absorbent core 1928 may comprises one or more channels, represented in FIG. 4 as the four channels 1926, 1926' and 1927, 1927'. Additionally or alternatively, the LMS 1950 may comprises one or more channels, represented in FIGS. 3-5 as channels 1949, 1949'. In some forms, the channels of the LMS 1950 may be positioned within the absorbent article 1900 such they aligned with, substantially aligned with, overlap, or at least partially overlap, the channels of the absorbent core 1928. These and other components of the absorbent articles will now be discussed in more details.

The topsheet 1924 is the part of the absorbent article that is directly in contact with the wearer's skin. The topsheet 1924 may be joined to the backsheet 1925, the core 1928 and/or any other layers as is known to those of skill in the art. Usually, the topsheet 1924 and the backsheet 1925 are joined directly to each other in some locations (e.g., on or close to the periphery of the article) and are indirectly joined together in other locations by directly joining them to one or more other elements of the absorbent article 1900.

The backsheet 1925 is generally that portion of the absorbent article 1900 positioned adjacent the garment-facing surface of the absorbent core 1928 and which prevents, or at least inhibits, the bodily exudates absorbed and contained therein from soiling articles such as bedsheets and undergarments. The backsheet 1925 is typically impermeable, or at least substantially impermeable, to liquids (e.g., urine, running BM), but permeable to vapors to allow the diaper to "breath". The backsheet may, for example, be or comprise a thin plastic film such as a thermoplastic film having a thickness of about 0.012 mm to about 0.051 mm. Example backsheet films include those manufactured by Tredegar Corporation, based in Richmond, Va., and sold under the trade name CPC2 film. Other suitable backsheet materials may include breathable materials which permit vapors to escape from the absorbent article 1900 while still preventing, or at least inhibiting, bodily exudates from passing through the backsheet 1925. Example breathable materials may include materials such as woven webs, nonwoven webs, and composite materials such as film-coated nonwoven webs, microporous films, and monolithic films.

The backsheet 1925 may be joined to the topsheet 1924, the absorbent core 1928, and/or any other element of the absorbent article 1900 by any attachment methods known to those of skill in the art. Suitable attachment methods are described above with respect to methods for joining the topsheet 1924 to other elements of the absorbent article 1900.

As used herein, the term "absorbent core" refers to the individual component of the absorbent article having the most absorbent capacity and that comprises an absorbent material. The absorbent core may comprise a core wrap or core bag (hereafter "core wrap") enclosing the absorbent material. The term "absorbent core" does not include the LMS or any other component of the absorbent article which is not either integral part of the core wrap or placed within the core wrap. The absorbent core may comprise, consist essentially of, or consist of, a core wrap, absorbent material as defined below, and glue enclosed within the core wrap. Pulp or air-felt may also be present within the core wrap and may form a portion of the absorbent material. The absorbent core periphery, which may be the periphery of the core wrap, may define any suitable shape, such as a "T," "Y," "hour-glass," or "dog-bone" shape, for example. An absorbent core periphery having a generally "dog bone" or "hour-glass" shape may taper along its width towards the middle or "crotch" region of the core. In this way, the absorbent core may have a relatively narrow width in an area of the absorbent core intended to be placed in the crotch region of an absorbent article.

The absorbent core 1928 of the present disclosure may comprise an absorbent material with a high amount of superabsorbent polymers (herein abbreviated as "SAP") enclosed within a core wrap. The SAP content may represent 70% to 100% or at least 70%, 75%, 80%, 85%, 90%, 95%, 99%, or 100% by weight of the absorbent material contained in the core wrap. The SAP useful with the present disclosure may include a variety of water-insoluble, but water-swellable polymers capable of absorbing large quantities of fluids. The core wrap is not considered as absorbent material for the purpose of assessing the percentage of SAP in the absorbent core. The remainder of the absorbent material in the core 1928 may be air-felt.

"Absorbent material" means a material which has some absorbency property or liquid retaining properties, such as SAP, cellulosic fibers as well as synthetic fibers. Typically, glues used in making absorbent cores have no absorbency properties and are not considered as absorbent material. The SAP content may be higher than 80%, for example at least 85%, at least 90%, at least 95%, at least 99%, and even up to and including 100% of the weight of the absorbent material contained within the core wrap, as stated above. This provides a relatively thin core compared to conventional cores typically comprising between 40-60% SAP, for example, and high content of cellulose fibers or airfelt. The absorbent material may comprise less than 15% or less than 10% weight percent of natural or synthetic fibers, less than 5% weight percent, less than 3% weight percent, less than 2% weight percent, less than 1% weight percent, or may even be substantially free of, or free of, natural and/or synthetic fibers, specifically reciting all 0.1% increments within the specified ranges and all ranges formed therein or thereby. The absorbent material may comprise little or no airfelt (cellulose) fibers, in particular the absorbent core may comprise less than 15%, 10%, 5%, 3%, 2%, 1% airfelt (cellulose) fibers by weight, or may even be substantially free of, or free of, cellulose fibers, specifically reciting all 0.1% increments within the specified ranges and all ranges formed therein or thereby.

The absorbent core 1928 may also comprise a generally planar top side and a generally planar bottom side. The core 1928 may have a longitudinal axis 80' corresponding substantially to the longitudinal axis 80 of the absorbent article, as seen from the top in a planar view as in FIG. 4. The absorbent material may be distributed in higher amount towards the front side than towards the rear side as more absorbency may be required at the front in particular articles. The absorbent material may have a non-uniform basis weight or a uniform basis weight across any portion of the core. The core wrap may be formed by two nonwoven materials, substrates, laminates, or other materials, 1916, 1916' which may be at least partially sealed along the sides of the absorbent core. The core wrap may be at least partially sealed along its front side, rear side, and two longitudinal sides so that substantially no absorbent material leaks out of the absorbent core wrap. The first material, substrate, or nonwoven 1916 may at least partially surround the second material, substrate, or nonwoven 1916' to form the core wrap. The first material 1916 may surround a portion of the second material 1916' proximate to the first and second side edges 1903 and 1904.

Cores comprising relatively high amount of SAP with various core designs are disclosed in U.S. Pat. No. 5,599,335 (Goldman), EP 1,447,066 (Busam), WO 95/11652 (Tanzer), U.S. Pat. Publ. No. 2008/0312622A1 (Hundorf), and WO 2012/052172 (Van Malderen).

The absorbent material may be one or more continuous layers present within the core wrap. Alternatively, the absorbent material may be comprised of individual pockets or stripes of absorbent material enclosed within the core wrap. In the first case, the absorbent material may be, for example, obtained by the application of a single continuous layer of absorbent material. The continuous layer of absorbent material, in particular of SAP, may also be obtained by combining two or more absorbent layers having discontinuous absorbent material application pattern, wherein the resulting layer is substantially continuously distributed across the absorbent particulate polymer material area, as disclosed in U.S. Pat. Appl. Publ. No. 2008/0312622A1 (Hundorf), for example. The absorbent core 1928 may comprise a first absorbent layer and a second absorbent layer. The first absorbent layer may comprise the first material 1916 and a first layer of absorbent material 1960, which may be 100% or less of SAP. The second absorbent layer may comprise the second material 1916' and a second layer of absorbent material 1960, which may also be 100% or less of SAP.

The fibrous thermoplastic adhesive material may be at least partially in contact with the absorbent material 1960 in the land areas and at least partially in contact with the materials 1916 and 1916' in the junction areas. This imparts an essentially three-dimensional structure to the fibrous layer of thermoplastic adhesive material, which in itself is essentially a two-dimensional structure of relatively small thickness, as compared to the dimension in length and width directions. Thereby, the fibrous thermoplastic adhesive material may provide cavities to cover the absorbent material in the land area, and thereby immobilizes this absorbent material, which may be 100% or less of SAP.

The core wrap may be made of a single substrate, material, or nonwoven folded around the absorbent material, or may comprise two (or more) substrates, materials, or nonwovens which are attached to another. Typical attachments are the so-called C-wrap and/or sandwich wrap. In a C-wrap, the longitudinal and/or transversal edges of one of the substrates are folded over the other substrate to form flaps. These flaps are then bonded to the external surface of the other substrate, typically by gluing. Other techniques may be used to form a core wrap. For example, the longitudinal and/or transversal edges of the substrates may be bonded together and then folded underneath the absorbent core 1928 and bonded in that position.

The core wrap may be at least partially sealed along all the sides of the absorbent core so that substantially no absorbent material leaks out of the core. By "substantially no absorbent material" it is meant that less than 5%, less than 2%, less than 1%, or about 0% by weight of absorbent material escape the core wrap. The term "seal" is to be understood in a broad sense. The seal does not need to be continuous along the whole periphery of the core wrap but may be discontinuous along part or the whole of it, such as formed by a series of seal points spaced on a line. A seal may be formed by gluing and/or thermal bonding.

The core wrap may also be formed by a single substrate which may enclose as in a parcel wrap the absorbent material and be sealed along the front side and rear side of the core and one longitudinal seal.

The absorbent article 1900 may comprise a pair of barrier leg cuffs 1934. Each barrier leg cuff may be formed by a piece of material which is bonded to the absorbent article so it can extend upwards from the inner surface of the absorbent article and provide improved containment of liquids and other bodily exudates approximately at the junction of the torso and legs of the wearer. The barrier leg cuffs 1934 are delimited by a proximal edge 1964 joined directly or indirectly to the topsheet 1924 and/or the backsheet 1925 and a free terminal edge 1966, which is intended to contact and form a seal with the wearer's skin. The barrier leg cuffs 1934 extend at least partially between the front waist edge 1910 and the rear waist edge 1912 of the absorbent article on opposite sides of the longitudinal axis 1980 and are at least present in the crotch region 1907. The barrier leg cuffs 1934 may be joined at the proximal edge 1964 with the chassis of the absorbent article by a bond 1965 which may be made by gluing, fusion bonding, or combination of other suitable bonding processes. The bond 1965 at the proximal edge 64 may be continuous or intermittent. The bond 1965 closest to the raised section of the leg cuffs 1934 delimits the proximal edge 1964 of the standing up section of the leg cuffs 1934.

The barrier leg cuffs 1934 may be integral with the topsheet 1924 or the backsheet 1925 or may be a separate material joined to the absorbent article's chassis. The material of the barrier leg cuffs 1934 may extend through the whole length of the diapers but may be "tack bonded" to the topsheet 1924 towards the front waist edge 1910 and rear waist edge 1912 of the absorbent article so that in these sections the barrier leg cuff material remains flush with the topsheet 1924.

Each barrier leg cuff 1934 may comprise one, two or more elastic strands or strips of film 1935 close to this free terminal edge 1966 to provide a better seal.

In addition to the barrier leg cuffs 1934, the absorbent article may comprise gasketing cuffs 1932, which are joined to the chassis of the absorbent article, in particular to the topsheet 1924 and/or the backsheet 1925 and are placed externally relative to the barrier leg cuffs 1934. The gasketing cuffs 1932 may provide a better seal around the thighs of the wearer. Each gasketing leg cuff may comprise one or more elastic strings 1933 or elastic elements in the chassis of the absorbent article between the topsheet 1924 and backsheet 1925 in the area of the leg openings. All or a portion of the barrier leg and/or gasketing cuffs may be treated with a lotion or skin care composition. The barrier leg cuffs may be constructed in a number of different configurations, including those described in U.S. Pat. App. Publ. No. 2012/0277713.

In a form, the absorbent article may comprise front ears 1946 and rear ears 1940. The ears may be an integral part of the chassis, such as formed from the topsheet 1924 and/or backsheet 1925 as side panel. Alternatively, as represented on FIG. 4, the ears (1946, 1940) may be separate elements attached by gluing, heat embossing, and/or pressure bonding. The rear ears 1940 may be stretchable to facilitate the attachment of the tabs 1942 to the landing zone 1944 and maintain the taped diapers in place around the wearer's waist. The rear ears 1940 may also be elastic or extensible to provide a more comfortable and contouring fit by initially conformably fitting the absorbent article to the wearer and sustaining this fit throughout the time of wear well past when absorbent article has been loaded with exudates since the elasticized ears allow the sides of the absorbent article to expand and contract.

One function of the LMS 1950 is to quickly acquire the fluid and distribute it to the absorbent core 1928 in an efficient manner. The LMS 1950 may comprise one or more layers, which may form a unitary layer or may remain as discrete layers which may be attached to each other. The LMS 1950 may comprise additional layers: a distribution layer 1954 and/or an acquisition layer 1952 disposed between the absorbent core and the topsheet, but the present disclosure is not limited to such a configuration.

The LMS 1950 may comprise SAP as this may slow the acquisition and distribution of the fluid. In other forms, the LMS may be substantially free (e.g., 80%, 85%, 90%, 95%, or 99% free of) or completely free of SAP. The LMS may also comprise one or more of a variety of other suitable types of materials, such as opened-cell foam, air-laid fibers, or carded, resin bonded nonwoven materials, for example. Suitable example LMSs are described in WO 2000/59430 (Daley), WO 95/10996 (Richards), U.S. Pat. No. 5,700,254 (McDowall), and WO 02/067809 (Graef), for example.

The distribution layer 1954 may comprise at least 50% or more by weight of cross-linked cellulose fibers, for example. The cross-linked cellulosic fibers may be crimped, twisted, or curled, or a combination thereof including crimped, twisted, and curled. This type of material is disclosed in U.S. Pat. Publ. No. 2008/0312622 A1 (Hundorf).

The acquisition layer 1952 may be disposed, for example, between the distribution layer 1954 and the topsheet 1924. The acquisition layer 1952 may be or may comprise a non-woven material, such as an SMS or SMMS material, comprising a spunbonded, a melt-blown and a further spunbonded layer or alternatively a carded chemical-bonded nonwoven. The acquisition layer 1952 may comprise air or wet-laid cellulosic, cross-linked cellulosic, or synthetic fibers, or blends thereof. The acquisition layer 1952 may comprise a roll-stock web of synthetic fibers (which may be processed to increase void space, such as by solid state formation), or a combination of synthetic and cellulosic fibers, bonded together to form a highloft material. Alternatively, the acquisition layer 1952 may comprise absorbent open cell foam. The nonwoven material may be latex bonded.

The LMS 1950 of the absorbent article 1900 may comprise channels that may generally enable better conformation of the absorbent article to the wearer's anatomy, leading to increased freedom-of-movement and reduced gapping. One or more of the channels of the LMS 1950 may be configured to work in concert with various channels in the absorbent core 1928, as discussed above. Furthermore, channels in the LMS 1950 may also provide increased void space to hold and distribute urine, BM or other bodily exudates within the absorbent article, leading to reduced leakage and skin contact. Channels in the LMS 1950 may also provide internal serviceable indicia, especially when highlighted via physical differences in texture, color, and/or pattern, to facilitate achieving the correct alignment of the absorbent article on a wearer. Thus, such physical differences may be, for example, visually and/or tactilely noticeable.

As stated previously, the material webs of the present invention may be utilized as a topsheet for a disposable absorbent article, examples of which include the sanitary napkin 1710 and diaper 1900 discussed heretofore.

The material webs of the present disclosure may be used as components of absorbent articles. More than one material web may be used in a single absorbent article. In such a context, the material webs may form at least a portion of: a topsheet; a topsheet and an acquisition layer; a topsheet and a distribution layer; an acquisition layer and a distribution layer; a topsheet of an absorbent article. The number of strata in a nonwoven web may also be determined by the nonwoven laminates' particular use.

In some forms, additional layers may be positioned between the topsheet and the absorbent core. For example, a secondary topsheet, acquisition layer, and/or distribution layer, each of which are known in the art, may be positioned between the topsheet and the absorbent core of the absorbent article.

Tests

Glass Transition Temperature and Melting Temperature

Tg and melting point are determined in accordance with ASTM D3418-15 for both the base matrix polymer and the neat melt-additive. When melt additive is not directly available, it can be collected from heat treated substrate using the extraction described in "Solvent Wash Procedure".

Filament Diameter and Denier Test

The diameter of filaments or fibers in a sample of a nonwoven substrate is determined by using a Scanning Electron Microscope (SEM) and image analysis software. A magnification of 500 to 10,000 times is chosen such that the filaments or fibers are suitably enlarged for measurement. The samples are sputtered with gold or a palladium compound to avoid electric charging and vibrations of the filaments or fibers in the electron beam. A manual procedure for determining the filament diameters is used. Using a mouse and a cursor tool, the edge of a randomly selected filament is sought and then measured across its width (i.e., perpendicular to filament direction at that point) to the other edge of the filament. For non-circular filaments or fibers, the area of the cross-section is measured using the image analysis software. The effective diameter is then calculated by calculating the diameter as if the found area was that of a circle. A scaled and calibrated image analysis tool provides the scaling to get actual reading in micrometers ($\mu$m). Several filaments or fibers are thus randomly selected across the sample of the nonwoven substrate using the SEM. At least two specimens from the nonwoven substrate are cut and tested in this manner. Altogether, at least 100 such measurements are made and then all data is recorded for statistical analysis. The recorded data is used to calculate average (mean) of the filament diameters, standard deviation of the filament diameters, and median of the filament diameters. Another useful statistic is the calculation of the amount of the population of filaments or fibers that is below a certain upper limit. To determine this statistic, the software is programmed to count how many results of the filament diameters are below an upper limit and that count (divided by total number of data and multiplied by 100%) is reported in percent as percent below the upper limit, such as percent below 1 micrometer diameter or %-submicron, for example.

If the results are to be reported in denier, then the following calculations are made.

$$\text{Filament Diameter in denier} = \text{Cross-sectional area (in m}^2\text{)} * \text{density (in kg/m}^3\text{)} * 9000 \text{ m} * 1000 \text{ g/kg}.$$

For round filaments or fibers, the cross-sectional area is defined by the equation:

$$A = \pi * (D/2)^2.$$

The density for polypropylene, for example, may be taken as 910 kg/m3.

Given the filament diameter in denier, the physical circular filament diameter in meters (or micrometers) is calculated from these relationships and vice versa. We denote the measured diameter (in microns) of an individual circular filament as D.

In case the filaments or fibers have non-circular cross-sections, the measurement of the filament diameter is determined as and set equal to the hydraulic diameter, as discussed above.

Mass-Average Diameter

The mass-average diameter of filaments is calculated as follows: mass average diameter, $$d_{mass} = \frac{\sum_{i=1}^{n}(m_i \cdot d_i)}{\sum_{i=1}^{n} m_i} = \frac{\sum_{i=1}^{n}(\rho \cdot V_i \cdot d_i)}{\sum_{i=1}^{n}(\rho \cdot V_i)} = \frac{\sum_{i=1}^{n}\left(\rho \cdot \frac{\pi d_i^2 \cdot \partial x}{4} \cdot d_i\right)}{\sum_{i=1}^{n}\left(\rho \cdot \frac{\pi d_i^2 \cdot \partial x}{4}\right)} = \frac{\sum_{i=1}^{n} d_i^3}{\sum_{i=1}^{n} d_i^2}$$

where
filaments in the sample are assumed to be circular/cylindrical,
$d_i$=measured diameter of the $i^{th}$ filament in the sample,
$\partial x$=infinitesimal longitudinal section of filament where its diameter is measured, same for all the filaments in the sample,
$m_i$=mass of the $i^{th}$ filament in the sample,
n=number of filaments whose diameter is measured in the sample
$\rho$=density of filaments in the sample, same for all the filaments in the sample
$V_i$=volume of the $i^{th}$ filament in the sample.

The mass-average filament diameter should be reported in μm.

Gravimetric Weight Loss Test

The Gravimetric Weight Loss Test can be used to determine the amount of lipid ester (e.g., GTS) in a nonwoven substrate of the present disclosure. One or more samples of the nonwoven substrate are placed, with the narrowest sample dimension no greater than 1 mm, into acetone at a ratio of 1 g nonwoven substrate sample per 100 g of acetone using a refluxing flask system. First, the sample is weighed before being placed into the reflux flask, and then the mixture of the sample and the acetone is heated to 60° C. for 20 hours. The sample is then removed and air dried for 60 minutes and a final weight of the sample is determined. The equation for calculating the weight percent lipid ester in the sample is:

weight % lipid ester=([initial mass of the sample– final mass of the sample]/[initial mass of the sample])×100%.

Presence of a Melt Additive

Presence of a melt additive (as opposed to a surface coating) is determined by comparison of non-heat activated substrate with and without solvent wash. Non activated regions can be identified using the "Determination of Activated Zones by FTIR/ATR" method as described previously and excised from the substrate for analysis. Approximately 2.0 grams needs to be collected.

An appropriate solvent is identified which is effective to dissolve the additive but will not swell the matrix or dissolve any further additive from the matrix. For GTS in PP, acetone is an appropriate solvent.

1.00 g±0.01 g of the non-heat activated substrate is weighed into a 500 mL flask and 100 mL of a solvent is added. The substrate with solvent is then stirred for 30 minutes at 900 rpm at 20° C. The solvent is decanted and the flask is refilled with a second 100 mL of solvent. The mixture is stirred again for 30 minutes at 900 rpm at 20° C. The solvent is decanted and the nonwoven is dried overnight at 40° C.

Two melt films are prepared, the first of the non-activated area unwashed, and a second of the non-activated substrate after solvent wash, for analysis. Melt film were prepare and analyzed as described in "Quantification of Total Melt-Additive Concentration by FTIR". FTIR transmission measurements are made on three (3) randomly selected sites from each of the washed and non-washed films to calculate the total concentration. Calculate and record the arithmetic mean of the triplicates separately, and record as Concentration Washed and Concentration Unwashed to the nearest 0.1%. Report the ratio of the Unwashed Concentration divided by the Washed Concentration. A ratio greater than indicates a surface coating instead of a melt additive was used.

The FTIR (reflectance and ATR) measurements of melt additives in a polymer matrix are quantified by peak normalization. One absorption band is selected which is attributed exclusively to the melt additive and must be free of interference from other components or impurities in the sample mixture. This signal is denoted as $E_1$. An example is the peak between 1806 cm$^{-1}$ and 1660 cm$^{-1}$ for the GTS. A second band is selected that which is attributed exclusively to the polymer matrix and must be free of interferences from the sample matrix or other impurities in the sample mixture. The signal is used to normalize for path length of the specific specimen. This signal is denoted as $E_2$. An example is the peak between 985 cm$^{-1}$ and 950 cm$^{-1}$ for polypropylene (PP). The FTIR methods described herein are written directed specifically toward these examples, GTS in PP, but one skilled in the art, can select analogous peaks to facilitate analysis of other melt additives and matrixes.

Quantification of Total Melt-Additive Concentration by FTIR

Total GTS in fibers and/or filaments, is measured using transmission FTIR (a suitable instrument is the Nicolet 6700, Thermo Scientific, or equivalent). Calibration was performed using standard films prepared from known mixtures of GTS in PP and can be used to quantify the total concentration of GTS on and within a fiber. All testing is performed in a conditioned room maintained at 23° C.±2 C.° and 50%±2% relative humidity. Samples are conditioned under the same conditions for 2 hours prior to testing.

Calibration Standards are prepared by mixing the base polymer (e.g. polypropylene) with the active GTS. A volume of 55 cm³ of each standard was prepared at a concentration of 0.0%, 0.4%, 1.2%, 2.0%, 4.0%, 12.0% and 20.0% wt/wt of GTS in PP. First the components were accurately weighed and then placed into a laboratory tumble mixer (a suitable mixer is the Turbula T2C available from Willy A. Bachofen AG Maschinenfabrik, or equivalent) and mixed for 10 min. Next the mixture was added to a laboratory kneader (a suitable instrument is a Haake Polydrive Mixer, Thermo Electron GmbH, or equivalent) and kneaded at 180° C. at 10 rpm for 2 min and then again at 60 rpm for an additional 8 min. After kneading, each mixture is ground (a suitable grinder is the Wanner C13.20sv or equivalent) before being pressed into a film.

One melt film was prepared for each concentration using a hot press (a suitable press is the Graseby Specac Hot Press, or equivalent). A standard mixture of 25 mg was placed between two aluminum foils and melted until the pressing form reached 175° C., pressed for 2.0 min with a 5000 kg weight and then cooled for 20 min in a water cooled form under no pressure. The resulting film should have a uniform thickness from 59 µm to 62 µm.

Transmission FTIR is performed on three different locations on each calibration film under the following conditions: 64 scans at a resolution of 1.0 and amplification of 1.0 from 550 to 4000 cm$^{-1}$. Background scans are performed before every new specimen. Two peaks were measured for quantification, one associated with the PP and the second associated with the GTS. Using an appropriate software, draw a baseline between 1025 cm$^{-1}$ and 950 cm$^{-1}$ and measure the vertical drop from highest peak between 985 cm$^{-1}$ and 950 cm$^{-1}$ wavenumbers. Secondly, draw a baseline between 1806 cm$^{-1}$ and 1660 cm$^{-1}$ and measure the vertical drop from highest peak between those two wavenumbers.

Calibration is performed using peak ratio normalization. Extinction E at a specific wave length $\lambda$ is defined as:

$$E(\lambda) = \varepsilon \cdot c \cdot d$$

with c=weight fraction of the absorbing substance; d=thickness of the radiated sample path length and $\varepsilon$=coefficient of absorption. For a two-component-system from substance A and substance B, the equation would be expressed as:

$$E(\lambda) = \varepsilon_A(\lambda) \cdot c_A \cdot d + \varepsilon_B(\lambda) \cdot c_B \cdot d$$

To eliminate contribution from the path length, a ratio of the area of two peaks can be used:

$$\frac{E_1(\lambda)}{E_2(\lambda)} = \frac{\varepsilon_{A,1}(\lambda) \cdot c_A \cdot d_p + \varepsilon_{B,1}(\lambda) \cdot c_B \cdot d_p}{\varepsilon_{A,2}(\lambda) \cdot c_A \cdot d_p + \varepsilon_{B,2}(\lambda) \cdot c_B \cdot d_p}$$

Here $E_1$ refers to the peak between 1660 and 1806 cm$^{-1}$ and $E_2$ refers to the peak between 950 and 985 cm$^{-1}$. Taking into account that in a two component system, the single weight fractions $\chi$ add up to 1, this gives:

$$\frac{E_1(\lambda)}{E_2(\lambda)} = \frac{\varepsilon_{A,1}(\lambda) \cdot c_A + \varepsilon_{B,1}(\lambda) \cdot (1 - c_A)}{\varepsilon_{A,2}(\lambda) \cdot c_A + \varepsilon_{B,2}(\lambda) \cdot (1 - c_A)}$$

Here the weight fraction of the component is independent of the path length. Plot the ratio of $E_1/E_2$ versus the concentration of the calibration sample and perform a least square linear fit. The calibration is defined as:

$$\frac{E_1}{E_2} = x \cdot c_{initial}$$

with x corresponding to a calibration coefficient used to relate the peak ratio to concentration as % GTS.

Analysis of a sample nonwoven is performed on 25 mg of nonwoven excised from the site of interest. Once again a film is prepared using a hot press with the specimen placed between two aluminum foils and melted until the pressing form reached 175° C., pressed for 2.0 min with a 5000 kg weight and then cooled for 20 min in a water cooled form under no pressure. The resulting film should have a uniform thickness from 59 µm to 62 µm.

Transmission FTIR is performed on three different locations on each specimen film using the identical conditions as the standards. Peak heights in the 1025 cm$^{-1}$ and 950 cm$^{-1}$ region and 1806 cm$^{-1}$ and 1660 cm$^{-1}$ region are collected in like fashion as the standards. The % GTS is calculated using the calibration coefficient derived above for the three replicates and reported as the arithmetic average to the nearest 0.1%.

Quantification of Heat Activated Zones via FTIR/ATR

GTS surface enrichment on fibers and/or filaments, is measured using Attenuated Total Reflection (ATR) FTIR (a suitable instrument is the Nicholet 6700, Thermo Scientific, or equivalent) utilizing both a Germanium and Diamond crystal. The instrument should be capable of correcting the ATR signal to match transmission FTIR signal in accordance with the Advanced ATR Correction Algorithm as described in Thermo Scientific Application Note 50581. The correction is applied as specified by the manufactures operating procedures. All testing is performed in a conditioned room maintained at 23° C.±2 C.° and 50%±2% relative humidity. Samples are conditioned under the same conditions for 2 hours prior to testing.

Surface enrichment of GTS is measured using FTIR ATR with both a germanium crystal and diamond crystal. Selecting the germanium crystal, the specimen is placed on the ATR stage with the site of interest centered beneath the crystal. The crystal is pressed against the specimen using the probe to a pressure of 68.9 N/mm$^2$. 64 scans are collected at a resolution of one data point per every 0.482 cm$^{-1}$, amplification of 1.0, 64 scans are collected at a resolution of one data point per every 0.482 cm$^{-1}$, amplification of 1.0, and 1 bounce measurement type, between a wave number of 550 cm$^{-1}$ to 4000 cm$^{-1}$. Between each measurement the crystal and plunger must be cleaned thoroughly with isopropanol to prevent carry-over from the previous analyses. After cleaning wait at least 10 min before starting a new measurement to ensure no residual isopropanol is present on the stage and crystal. Background spectra, using the parameters specified above, were collected every 15 minutes. This background spectrum is subtracted from each measured sample spectra. A spectrum is collected on three different but equivalent sites for a total of 3 spectra. Spectra were repeated using this protocol for both the germanium and diamond crystals. Two peaks were measured for quantification, one associated with the PP and the second associated with the GTS.

The ATR signal can be corrected to match transmission FTIR signal by application of the following equation (equation was derived from Thermo Scientific Application note 50581):

$$A = -\log_{10(ART)} = (\log_{10} e) \frac{n_2}{n_1} \frac{E_0^2}{\cos\emptyset} \frac{d_p}{2} \alpha$$

where:
A=ATR intensity
$E_0$=electric fields of the evanescent wave at the boundary
$\alpha$=absorption coefficient per unit thickness of sample
$d_p$=penetration depth
$n_1$=refractive index of the crystal
$n_2$=refractive index of the sample
$\emptyset$=incident angle The penetration depth ($d_p$) for each crystal is calculated using the following equation:

$$d_p = \frac{\lambda}{2\pi n_{Crystal} \sqrt{\sin^2(\theta) - \left(\frac{n_{Sample}}{n_{Crystal}}\right)^2}}$$

with n is the refractive index, θ is the incident angle, and λ is the incident wave length. The refractive index of the sample is taken as 1.49 for PP and PE. For example, a germanium crystal (refractive index=4.0 and incident angle=42°) would give 0.41 μm penetration and a diamond crystal (refractive index=2.4 and incident angle=42°) would give 1.51 μm penetration. Values must be calculated based on the specific configuration of the instrument used.

Using an appropriate software draw a baseline between 1806 cm$^{-1}$ and 1660 cm$^{-1}$ and measure the vertical drop from highest peak between those two wave numbers. This is $E_1$. Secondly, draw a baseline between 1025 cm$^{-1}$ and 950 cm$^{-1}$ and measure the vertical drop from highest peak between 985 cm$^{-1}$ and 950 cm$^{-1}$ wave numbers. This is $E_2$. Quantification is performed with the calibration coefficient x as determined herein from the "Quantification of Total Melt-Additive Concentration by FTIR" method using the equation:

$$c = \left(\frac{E_1}{E_2}\right)/x$$

The % GTS is calculated for the three replicates and reported as the arithmetic average to the nearest 0.1%.

Contact Angle Method

Contact angles on substrates are determined using ASTM D7490-13 modified with the specifics as describe herein, using a goniometer and appropriate image analysis software (a suitable instrument is the FTA200, First Ten Angstroms, Portsmouth, Va., or equivalent) fitted with a 1 mL capacity, gas tight syringe with a No. 27 blunt tipped stainless steel needle. One test fluid is used: Type II reagent water (distilled) in accordance with ASTM Specification D1193-99. All testing is to be performed at about 23° C.±2 C.° and a relative humidity of about 50%±2%.

A 50 mm by 50 mm specimen to be tested is removed from the topsheet of the article being tested taking care to not touch the region of interest or otherwise contaminate the surface during harvesting or subsequent analysis. Condition the samples at about 23° C.±2 C.° and a relative humidity of about 50%±2% for 2 hours prior to testing.

Set up the goniometer on a vibration-isolation table and level the stage according to the manufacturer's instructions. The video capture device must have an acquisition speed capable of capturing at least 10-20 images from the time the drop hits the surface of the specimen to the time it cannot be resolved from the specimen's surface. A capture rate of 900 images/sec is typical. Depending on the hydrophobicity/hydrophilicity of the specimen, the drop may or may not rapidly wet the surface of the sample. In the case of slow acquisition, the images should be acquired until 2% of the volume of the drop is absorbed into the specimen. If the acquisition is extremely fast, the first resolved image should be used if the second image shows more than 2% volume loss.

Place the specimen on the goniometer's stage and adjust the hypodermic needle to the distance from the surface recommended by the instrument's manufacturer (typically 3 mm). If necessary adjust the position of the specimen to place the target site under the needle tip. Focus the video device such that a sharp image of the drop on the surface of the specimen can be captured. Start the image acquisition. Deposit a 5 μL±0.1 μL drop onto the specimen. If there is visible distortion of the drop shape due to movement, repeat at a different, but equivalent, target location. Make two angle measurements on the drop (one on each drop edge) from the image at which there is a 2% drop volume loss. If the contact angles on two edges are different by more than 4°, the values should be excluded and the test repeated at an equivalent location on the specimen. Identify five additional equivalent sites on the specimen and repeat for a total of 6 measurements (12 angles). Calculate the arithmetic mean for this side of the specimen and report to the nearest 0.01°. In like fashion, measure the contact angle on the opposite side of the specimen for 6 drops (12 angles) and report separately to the nearest 0.01°.

SEM Method for Determining Contact Angle on Fibers and/or Filaments

When a contact angle on a single fiber or filament is desired, the SEM Method for determining contact angle can be utilized. A rectangular specimen measuring 1 cm×2 cm is cut from the topsheet of a disposable absorbent product taking care not to touch the surface of the specimen or to disturb the structure of the material. The specimen shall be inclusive of any heat activated zones identified via the Determination of Activated Zones by FTIR/ATR test method described heretofore. To the extent that additional heat activated zones lie outside of the specimen, additional specimens shall be obtained to accommodate all of the identified heat activated zones. The length of the specimen (2 cm) is aligned with a longitudinal centerline of the article. The specimen is handled gently by the edges using forceps and is mounted flat with the skin-facing side up on an SEM specimen holder using double-sided tape. The specimen is sprayed with a fine mist of water droplets generated using a small hobby air-brush apparatus. The water used to generate the droplets is distilled deionized water with a resistivity of at least 18 MΩ-cm. The airbrush is adjusted so that the droplets each have a volume of about 2 pL. Approximately 0.5 mg of water droplets are evenly and gently deposited onto the specimen. Immediately after applying the water droplets, the mounted specimen is frozen by plunging it into liquid nitrogen. After freezing, the sample is transferred to a Cryo-SEM prep chamber at −150° C., coated with Au/Pd, and transferred into Cryo-SEM chamber at −150° C. A Hitachi S-4700 Cry-SEM or equivalent instrument is used to obtain high-resolution images of the droplets on the fibers and/or filaments. Droplets are randomly selected, though a droplet is suitable to be imaged only if it is oriented in the microscope such that the projection of the droplet extending from the fiber surface is approximately maximized. This is further discussed with regard to FIGS. 6A-9B. The contact angle between the droplet and the fiber is determined directly from the images taken as is shown via lines 3700A, 3700B, 3800A, 3800B, 3900A, 3900B, 4000A, and 4000B. Twenty separate droplets are imaged from which forty contact angle measurements are performed (one on each side of each imaged droplet), and the arithmetic average of these forty contact angle measurements is calculated and reported as the contact angle for that specimen.

Figure 9A:
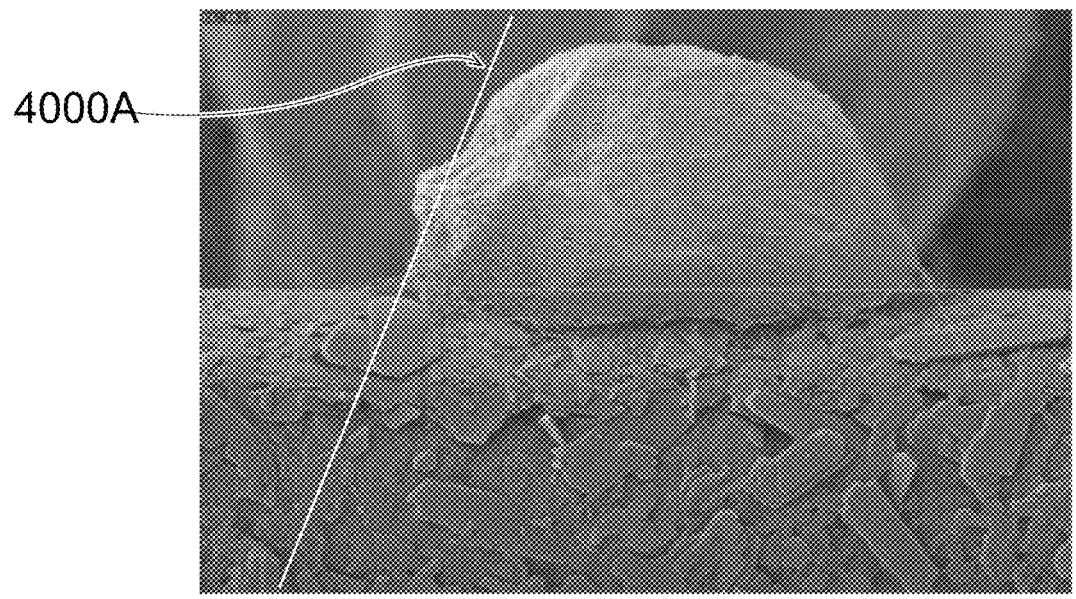
Figure 9B:
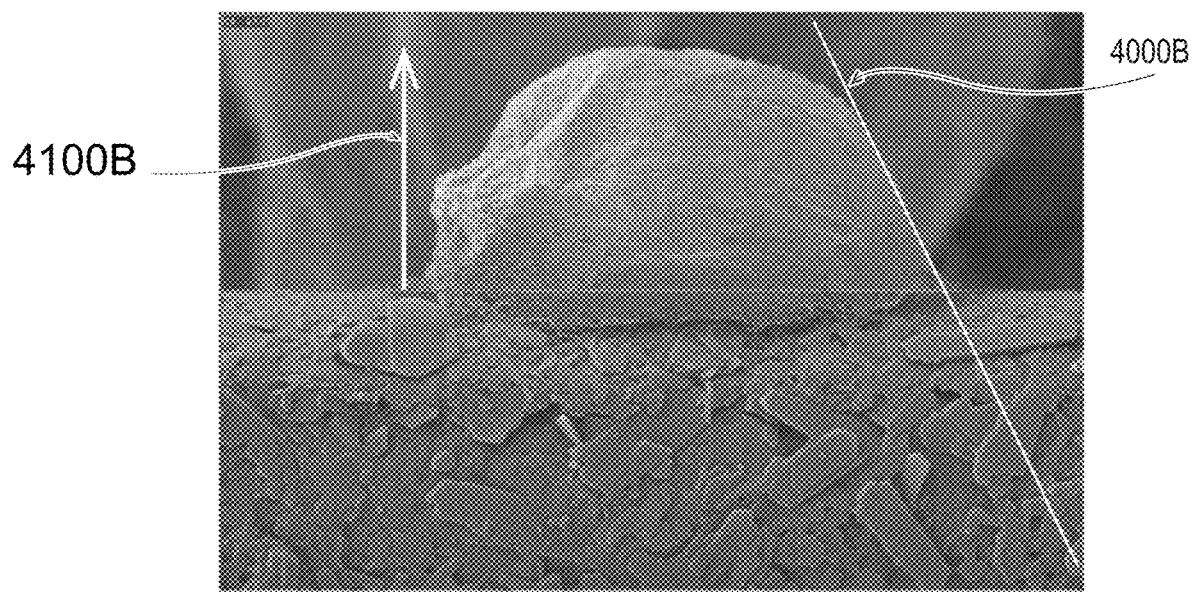

Examples of images are provided with regard to FIGS. 6A-9B. FIGS. 6A-7B are exemplary images depicting water droplets cryogenically frozen on fibers and/or filaments upon which no composition has been applied. FIGS. 8A-9B are exemplary images depicting water droplets cryogenically frozen on fibers and/or filaments upon which composition has been applied. As noted previously, the projection of the droplet should be maximized to ensure that the appropriate contact angle is measured. An exemplary droplet projection 4100B is shown in FIG. 9B.

Differential Scanning Calorimetry:

All tests were performed on a DSC Q 2000 (TA Instruments).

DSC was performed as described in DIN EN ISO 11357 with the following particulars: DSC scans were carried out with 2 full heating and 1 cooling runs from −40° C. to 200° C. for the master batches (and additive/PP blends in general) and from −60° C. to 80° C. for the pure additives with heating and cooling rates of 10 K/min. Between the heating and cooling runs, the samples were held for 180 seconds at isothermal conditions. All measurements were performed under constant Helium flow (as purge gas) of 20 ml/min. The second heating run was used to determine the onset of melting and the melting temperature. The melting temperature is determined as the minimum of the melting peak. The onset of melting is determined as the crossing point between the tangent through the crossing point of the melting peak and the extrapolated baseline.

Molecular Weight

Gel Permeation Chromatography (GPC) to obtain Weight-average Molar Mass (Mw) can be performed using Multi-Angle Light Scattering Detection (GPC-MALS) with a in line Interometric Refractometer. A suitable system would be a DAWN DSP Laser Photometer and Optilab DSP Interferometric Refractometer (Wyatt Technology) or equivalent. The solvent must be chosen, dependent on the polymer to be analyzed, to assure complete solubilization of the sample. Also the GPC columns must be chosen such that the polymer elutes within the linear response region of the column, away from the total exclusion and total inclusion volume. Weight-average Molar Mass (Mw) was calculated using the Zimm fit method.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A permeable nonwoven web having a first surface and a second surface with a thickness defined by the first surface and the second surface, the nonwoven web further comprising:
   a plurality of fibers and/or filaments, wherein each of the plurality of fibers and/or filaments comprise a first constituent polymer matrix which forms an outer surface of each of the fibers and/or filaments, and wherein the first constituent polymer matrix comprises a hydrophilic melt additive and/or a tactile modifying melt additive, and wherein the hydrophilic melt additive and/or tactile modifying melt additive blooming is present on the outer surface of the fiber and/or filaments only at one or both of the following areas: at a plurality of discrete junctions between the fibers and/or filaments; or at a plurality of discrete localized areas through the thickness of the nonwoven web.

2. The permeable nonwoven web of claim 1, wherein a glass transition temperature of the first constituent polymer matrix is less than 25 degrees C.

3. The permeable nonwoven web of claim 2, wherein the glass transition temperature of the first constituent polymer matrix is less than 15 degrees C.

4. The permeable nonwoven web of claim 1, wherein the hydrophilic melt additive and/or tactile modifying melt additive has a melting temperature of greater than 25 degrees C.

5. The permeable nonwoven web of claim 1, wherein each of the fibers and/or filament comprise bi-component fibers arranged in a sheath-core configuration, wherein the first constituent polymer matrix comprises the sheath and a second constituent polymer matrix comprises the core, and wherein the glass transition temperature of the first constituent polymer matrix is less than the glass transition temperature of the second constituent polymer matrix.

6. The permeable nonwoven web of claim 5, wherein the plurality of fibers and/or filaments are staple length fibers.

7. The permeable nonwoven web of claim 5, wherein a glass transition temperature of the second constituent polymer matrix is greater than 25 degrees C.

8. The permeable nonwoven web of claim 5, wherein a glass transition temperature of the second constituent polymer matrix is greater than 40 degrees C.

9. The permeable nonwoven web of claim 5, wherein a glass transition temperature of the second constituent polymer matrix is greater than a glass transition temperature of the first polymer matrix.

10. The permeable nonwoven web of claim 5, wherein a melt temperature of the second constituent polymer matrix is between 20 degrees C. to 50 degrees C. higher than a melt temperature of the first constituent polymer matrix.

11. The permeable nonwoven web of claim 5, wherein the melt additive blooming is present on the outer surface of the fibers and/or filaments at a plurality of junctions between the fibers and/or filaments.

12. The permeable nonwoven web of claim 11, wherein the permeable nonwoven web is air through bonded.

13. The permeable nonwoven web of claim 5, wherein the melt additive blooming is present on the outer surface of the fibers and/or filaments at a plurality of localized areas through the thickness of the nonwoven web.

14. The permeable nonwoven web of claim 5, wherein the hydrophilic and/or tactile modifying melt additive has a molecular weight of at least 700 g/mol.

15. The permeable nonwoven web of claim 5, wherein a weight ratio of the first constituent polymer matrix to the second constituent polymer matrix is between 50/50 to 20/80.

16. An absorbent article comprising a topsheet, a backsheet, and an absorbent core disposed between the topsheet and the backsheet, the absorbent article further comprising the permeable nonwoven web of claim 5 disposed between the topsheet and the absorbent core.

17. The permeable nonwoven web of claim 1, wherein the melt additive blooming has a lower contact angle than the first constituent polymer as measured by the SEM Method for determining contact angle.

18. A permeable nonwoven web having a first surface and an opposing second surface, and a thickness defined by the first surface and the second surface, the permeable nonwoven web further comprising:
- a plurality of bi-component staple fibers, each of the plurality of bi-component staple fibers being arranged in a core-sheath arrangement, the sheath comprising a first constituent polymer matrix and the core comprising a second constituent polymer matrix, wherein a melting temperature of the second constituent polymer matrix is between 20 degrees C. to 50 degrees C. higher than a melting temperature of the first constituent polymer matrix;
- a hydrophilic and/or tactile modifying melt additive blended with the first constituent polymer matrix;
- a plurality of discrete bloom areas disposed through the thickness of the permeable nonwoven web, the plurality of bloom areas being disposed on an outer surface of the sheath, and wherein the plurality of discrete bloom areas are present only at one or both of the following areas: at a plurality of discrete junctions between the bi-component staple fibers; or at a plurality of discrete localized areas through the thickness of the nonwoven web.

\* \* \* \* \*